US006011048A

United States Patent [19]
Mathvink et al.

[11] Patent Number: 6,011,048
[45] Date of Patent: Jan. 4, 2000

[54] THIAZOLE BENZENESULFONAMIDES AS β3 AGONISTS FOR TREATMENT OF DIABETES AND OBESITY

[75] Inventors: Robert J. Mathvink, Red Bank; Emma R. Parmee, Highland Park; Samuel Tolman, Jersey City; Ann E. Weber, Scotch Plains, all of N.J.

[73] Assignee: Merck & Co., Inc., Rahway, N.J.

[21] Appl. No.: 09/007,363

[22] Filed: Jan. 15, 1998

Related U.S. Application Data

[60] Provisional application No. 60/036,760, Jan. 28, 1997.
[51] Int. Cl.[7] .......................... C07D 417/10; A61K 31/44
[52] U.S. Cl. .................... 514/342; 546/269.7; 546/256; 514/333
[58] Field of Search .......................... 514/342; 546/269.7

[56] References Cited

U.S. PATENT DOCUMENTS

| | | | |
|---|---|---|---|
| 5,451,677 | 9/1995 | Fisher et al. | 546/130 |
| 5,561,142 | 10/1996 | Fisher et al. | 514/312 |
| 5,705,515 | 1/1998 | Fisher et al. | 514/365 |

FOREIGN PATENT DOCUMENTS

| | | |
|---|---|---|
| 0 091 749 | 10/1983 | European Pat. Off. . |
| 0 611 003 | 8/1994 | European Pat. Off. . |
| WO 95/29159 | 11/1995 | WIPO . |

*Primary Examiner*—Jane Fan
*Attorney, Agent, or Firm*—Mollie M. Yang; David L. Rose

[57] ABSTRACT

Thiazole substituted benzenesulfonamides are $\beta_3$ adrenergic receptor agonists with very little $\beta_1$ and $\beta_2$ adrenergic receptor activity and as such the compounds are capable of increasing lipolysis and energy expenditure in cells. The compounds thus have potent activity in the treatment of Type II diabetes and obesity. The compounds can also be used to lower triglyceride levels and cholesterol levels or raise high density lipoprotein levels or to decrease gut motility. In addition, the compounds can be used to reduced neurogenic inflammation or as antidepressant agents. The compounds are prepared by coupling an aminoalkylphenyl-sulfonamide with an appropriately substituted epoxide. Compositions and methods for the use of the compounds in the treatment of diabetes and obesity and for lowering triglyceride levels and cholesterol levels or raising high density lipoprotein levels or for decreasing gut motility are also disclosed.

10 Claims, No Drawings

THIAZOLE BENZENESULFONAMIDES AS β3 AGONISTS FOR TREATMENT OF DIABETES AND OBESITY

CROSS REFERENCE TO RELATED APPLICATIONS

This application is based on, and claims priority from, provisional application No. 60/036,760 filed Jan. 28, 1997.

BACKGROUND OF THE INVENTION

β-Adrenoceptors have been subclassified as $\beta_1$ and $\beta_2$ since 1967. Increased heart rate is the primary consequence of $\beta_1$-receptor stimulation, while bronchodilation and smooth muscle relaxation typically result from $\beta_2$ stimulation. Adipocyte lipolysis was initially thought to be solely a $\beta_1$-mediated process. However, more recent results indicate that the receptor mediating lipolysis is atypical in nature. These atypical receptors, later called $\beta_3$-adrenoceptors, are found on the cell surface of both white and brown adipocytes where their stimulation promotes both lipolysis (breakdown of fat) and energy expenditure.

Early developments in this area produced compounds with greater agonist activity for the stimulation of lipolysis ($\beta_3$ activity) than for stimulation of atrial rate ($\beta_1$) and tracheal relaxation ($\beta_2$). These early developments disclosed in Ainsworth et al., U.S. Pat. Nos. 4,478,849 and 4,396,627, were derivatives of phenylethanolamines.

Such selectivity for $\beta_3$-adrenoceptors could make compounds of this type potentially useful as antiobesity agents. In addition, these compounds have been reported to show antihyperglycemic effects in animal models of non-insulin-dependent diabetes mellitus.

A major drawback in treatment of chronic diseases with $\beta_3$ agonists is the potential for stimulation of other β-receptors and subsequent side effects. The most likely of these include muscle tremor ($\beta_2$) and increased heart rate ($\beta_1$). Although these phenylethanolamine derivatives do possess some $\beta_3$ selectivity, side effects of this type have been observed in human volunteers. It is reasonable to expect that these side effects resulted from partial $\beta_1$ and/or $\beta_2$ agonism.

More recent developments in this area are disclosed in Ainsworth et al., U.S. Pat. No. 5,153,210, Caulkett et al., U.S. Pat. No. 4,999,377, Alig et al., U.S. Pat. No. 5,017,619, Lecount et al., European Patent 427480 and Bloom et al., European Patent 455006.

Even though these more recent developments purport to describe compounds with greater $\beta_3$ selectivity over the $\beta_1$ and $\beta_2$ activities, this selectivity was determined using rodents, in particular, rats as the test animal. Because even the most highly selective compounds, as determined by these assays, still show signs of side effects due to residual $\beta_1$ and $\beta_2$ agonist activity when the compounds are tested in humans, it has become apparent that the rodent is not a good model for predicting human $\beta_3$ selectivity.

Recently, assays have been developed which more accurately predict the effects that can be expected in humans. These assays utilize cloned human $\beta_3$ receptors which have been expressed in Chinese hamster ovary cells. See Emorine et al, *Science,* 1989, 245:1118–1121; Liggett, *Mol. Pharmacol.,* 1992, 42:634–637; and Grannemann et al., *Mol. Pharmacol.,* 1992, 42: 964–970. The agonist and antagonist effects of the various compounds on the cultivated cells provide an indication of the antiobesity and antidiabetic effects of the compounds in humans.

U.S. Pat. No. 5,451,677 discloses selective β3 agonists of the formula:

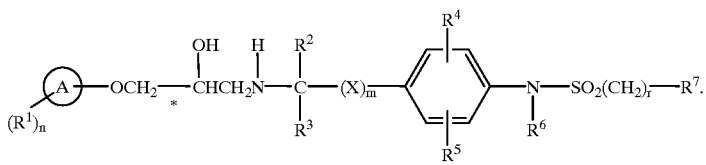

U.S. Pat. No. 5,561,142 published Nov. 2, 1995 discloses selective β3 agonists of the formula

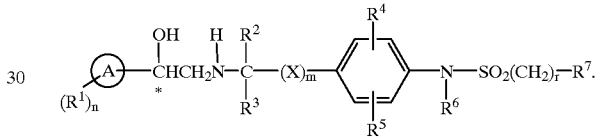

Compounds of the present invention that are within the generic disclosure of U.S. Pat. No. 5,561,142 represent a novel selection thereof.

SUMMARY OF THE INVENTION

The instant invention is concerned with thiazole substituted benzenesulfonamides which are useful as antiobesity and antidiabetic compounds. Thus, it is an object of this invention to describe such compounds. It is a further object to describe the specific preferred stereoisomers of the substituted sulfonamides. A still further object is to describe processes for the preparation of such compounds. Another object is to describe methods and compositions which use the compounds as the active ingredient thereof. Further objects will become apparent from reading the following description.

DESCRIPTION OF THE INVENTION

The present invention provides compounds having the formula I:

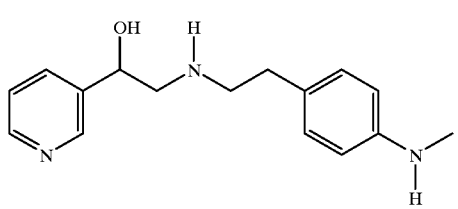

-continued

[structure: 4-(methylsulfonyl)phenyl-thiazole-X-A(R¹)ₘ]

wherein
X is
(1) a bond,
(2) $C_1$–$C_3$ alkylene, optionally substituted with 1 or 2 groups selected from methyl and halogen,
(3) $C_1$–$C_3$ alkylene wherein said alkylene contains an oxygen, optionally substituted with 1 or 2 groups selected from methyl and halogen;

m is
0 to 5;

A is
(1) phenyl,
(2) a 5 or 6-membered heterocyclic ring with from 1 to 4 heteroatoms selected from oxygen, sulfur and nitrogen,
(3) a benzene ring fused to a $C_5$–$C_{10}$ carbocyclic ring,
(4) a 5 or 6-membered heterocyclic ring with from 1 to 4 heteroatoms selected from oxygen, sulfur and nitrogen fused to a 5 or 6-membered heterocyclic ring with from 1 to 4 heteroatoms selected from oxygen, sulfur and nitrogen, or
(5) a 5 or 6-membered heterocyclic ring with from 1 to 4 heteroatoms selected from oxygen, sulfur and nitrogen fused to a $C_5$–$C_{10}$ carbocyclic ring;

$R^1$ is
(1) $C_1$–$C_{10}$ alkyl optionally substituted with up to 5 groups selected from
  (a) hydroxy,
  (b) halogen,
  (c) cyano,
  (d) $QR^2$,
  (e) $C_3$–$C_8$ cycloalkyl,
  (f) A optionally substituted with up to 5 groups selected from halogen, $C_1$–$C_{10}$ alkyl and $C_1$–$C_{10}$ alkoxy,
  (g) $Q'COR^3$,
  (h) $S(O)_nR^3$, where n is 0 to 2,
  (i) $NR^2SO_2R^3$,
  (j) $NR^2CO_2R^2$, and
  (k) $CO_2R^2$,
(2) $C_3$–$C_8$ cycloalkyl,
(3) oxo,
(4) halogen,
(5) cyano,
(6) $QR^2$,
(7) $S(O)_nR^3$, where n is 0 to 2,
(8) $Q'COR^3$,
(9) $NR^2SO_2R^3$,
(10) $NR^2CO_2R^2$,
(11) A optionally substituted with up to 5 groups independently selected from
  (a) $R^2$,
  (b) $QR^2$,
  (c) halogen, and
  (d) oxo; or
(12) $CO_2R^2$;

$R^2$ is
(1) hydrogen,
(2) $C_1$–$C_{10}$ alkyl optionally substituted with up to 5 groups selected from
  (a) hydroxy,
  (b) halogen,
  (c) $CO_2R^4$,
  (d) $S(O)_n$-$C_1$–$C_{10}$ alkyl, where n is 0 to 2,
  (e) $C_3$–$C_8$ cycloalkyl,
  (f) $C_1$–$C_{10}$ alkoxy, and
  (g) A optionally substituted with up to 5 groups selected from halogen, $C_1$–$C_{10}$ alkyl and $C_1$–$C_{10}$ alkoxy,
(3) $C_3$–$C_8$ cycloalkyl, or
(4) A optionally substituted with up to 5 groups selected from
  (a) halogen,
  (b) nitro,
  (c) oxo,
  (d) $NR^4R^4$,
  (e) $C_1$–$C_{10}$ alkoxy,
  (f) $S(O)_n$-$C_1$–$C_{10}$ alkyl where n is 0 to 2, and
  (g) $C_1$–$C_{10}$ alkyl optionally substituted with up to 5 groups selected from hydroxy, halogen, $CO_2R^4$, $S(O)_n$-$C_1$–$C_{10}$ alkyl, where n is 0 to 2, $C_3$–$C_8$ cycloalkyl, $C_1$–$C_{10}$ alkoxy, and A optionally substituted with up to 5 groups selected from halogen, $C_1$–$C_{10}$ alkyl and $C_1$–$C_{10}$ alkoxy;

$R^3$ is
(1) $R^2$ or
(2) $NR^2R^2$;

$R^4$ is
(1) H, or
(2) $C_1$–$C_{10}$ alkyl;

Q is
(1) $N(R^2)$,
(2) O or
(3) $S(O)n$, and n is 0 to 2;

Q' is
(1) $N(R^2)$,
(2) O or
(3) a bond; or a pharmaceutically acceptable salt thereof, or a prodrug thereof.

One subset of compounds of formula I provides compounds wherein
X is
(1) a bond,
(2) $CH_2$
(3) $CH_2O$, wherein C is attached to thiazole, and O is attached to A;

Another subset of compounds of formula I provides compounds wherein
$R^1$ is
(1) $C_1$–$C_{10}$ alkyl optionally substituted with up to 5 halogens;
(2) halogen,
(3) $QR^2$,
(4) $Q'COR^3$,
(5) phenyl;

$R^2$ is
(1) hydrogen,
(2) $C_1$–$C_{10}$ alkyl optionally substituted with up to 5 halogens;

R³ is
- (1) $C_1$–$C_{10}$ alkyl; and

Q is
- (1) O.

There is one subset of compounds of formula I wherein the thiazolyl moiety is attached to the benzenesulfonamide moiety via the carbon at the 2 position (C2) of the thiazole ring. There is another subset of compounds of formula I wherein the thiazolyl moiety is attached to X, or where X is a bond, directly to A via the carbon at the 2 position of the thiazole ring. Preferably, either the benzenesulfonamide moiety or X (or A, if X is a bond) is attached to the C2 of the thiazole ring, and the other to the C4 positions of the thiazole ring.

Another subset of compounds of formula I provides compounds wherein A is selected from phenyl, naphthyl, a 5 or 6-membered heterocyclic ring with from 1 to 4 heteroatoms selected from oxygen, sulfur and nitrogen fused to a benzene ring, and a 5 or 6-membered heterocyclic ring with from 1 to 4 heteroatoms selected from oxygen, sulfur and nitrogen. Preferably, A is selected from phenyl, naphthyl, thienyl, pyridinyl, benzothienyl, quinolinyl, indolyl, and benzofuranyl.

In a preferred embodiment of compounds of formula I
X is
- (1) a bond,
- (2) $CH_2$,
- (3) $CH_2O$, wherein C is attached to thiazole, and O is attached to A;

m is
- 0 to 5;

A is
- (1) phenyl,
- (2) a 5 or 6-membered heterocyclic ring with from 1 to 4 heteroatoms selected from oxygen, sulfur and nitrogen,
- (3) a benzene ring fused to a $C_5$–$C_{10}$ carbocyclic ring,
- (4) a 5 or 6-membered heterocyclic ring with from 1 to 4 heteroatoms selected from oxygen, sulfur and nitrogen fused to a 5 or 6-membered heterocyclic ring with from 1 to 4 heteroatoms selected from oxygen, sulfur and nitrogen, or
- (5) a 5 or 6-membered heterocyclic ring with from 1 to 4 heteroatoms selected from oxygen, sulfur and nitrogen fused to a $C_5$–$C_{10}$ carbocyclic ring;

R¹ is
- (1) $C_1$–$C_{10}$ alkyl optionally substituted with up to 5 halogens;
- (2) halogen,
- (3) $QR^2$,
- (4) $Q'COR^3$,
- (5) phenyl;

R² is
- (1) hydrogen,
- (2) $C_1$–$C_{10}$ alkyl optionally substituted with up to 5 halogens;

R³ is
- (1) $C_1$–$C_{10}$ alkyl; and

Q is
- (1) O; or
a pharmaceutically acceptable salt thereof.

In a more preferred embodiment are compounds of formula I wherein
X is
- (1) a bond,
- (2) $CH_2$,
- (3) $CH_2O$, wherein C is attached to thiazole, and O is attached to A;

m is
- 0 to 5;

A is
- (1) phenyl,
- (2) a 5 or 6-membered heterocyclic ring with from 1 to 4 heteroatoms selected from oxygen, sulfur and nitrogen,
- (3) naphthyl, or
- (4) a 5 or 6-membered heterocyclic ring with from 1 to 4 heteroatoms selected from oxygen, sulfur and nitrogen fused to a benzene ring;

R¹ is
- (1) $C_1$–$C_{10}$ alkyl optionally substituted with up to 5 halogens;
- (2) halogen,
- (3) $QR^2$,
- (4) $Q'COR^3$,
- (5) phenyl;

R² is
- (1) hydrogen,
- (2) $C_1$–$C_{10}$ alkyl optionally substituted with up to 5 halogens;

R³ is
- (1) $C_1$–$C_{10}$ alkyl; and

Q is
- (1) O; and either the benzenesulfonamide moiety or X (or A, if X is a bond) is attached to the C2 of the thiazole ring, and the other to the C4 positions of the thiazole ring; or a pharmaceutically acceptable salt thereof.

Compounds of the present invention that are within the generic structure disclosed in U.S. Pat. No. 5,561,142 represent a novel selection thereof. The present compounds are potent β3 agonists, and have improved oral bioavailability in animals.

Representative antiobesity and antidiabetic compounds of the present invention include the following:

1. N-[4-[2-[[2-hydroxy-2-(3-pyridinyl)ethyl]amino]ethyl]phenyl]-4-[4-(2-naphthylmethyl)thiazol-2-yl]benzenesulfonamide;
2. N-[4-[2-[[2-hydroxy-2-(pyridin-3-yl)ethyl]amino]ethyl]phenyl]-4-[4-(trifluoromethyl)phenyl]thiazol-2-yl]benzenesulfonamide;
3. N-[4-[2-[[2-hydroxy-2-(pyridin-3-yl)ethyl]amino]ethyl]phenyl]-4-[4-(trifluoromethoxy)phenyl]thiazol-2-yl]benzenesulfonamide;
4. N-[4-[2-[[2-hydroxy-2-(pyridin-3-yl)ethyl]amino]ethyl]phenyl]-4-[4-(3,4-difluorophenylmethyl)thiazol-2-yl]benzenesulfonamide;
5. N-[4-[2-[[2-hydroxy-2-(pyridin-3-yl)ethyl]amino]ethyl]phenyl]-4-[4-(3-pyridyl)thiazol-2-yl]benzenesulfonamide;
6. N-[4-[2-[[2-hydroxy-2-(pyridin-3-yl)ethyl]amino]ethyl]phenyl]-4-[4-(4-fluorophenylmethyl)thiazol-2-yl]benzenesulfonamide;
7. N-[4-[2-[[2-hydroxy-2-(pyridin-3-yl)ethyl]amino]ethyl]phenyl]-4-[4-(3,4-difluorophenyl)thiazol-2-yl]benzenesulfonamide;
8. N-[4-[2-[[2-hydroxy-2-(pyridin-3-yl)ethyl]amino]ethyl]phenyl]-4-[4-(trifluoromethyl)phenylmethyl]thiazol-2-yl]benzenesulfonamide;

9. N-[4-[2-[[2-hydroxy-2-(pyridin-3-yl)ethyl]amino]ethyl]phenyl]-4-[4-(2-pyridyl)thiazol-2-yl]benzenesulfonamide;
10. N-[4-[2-[[2-hydroxy-2-(pyridin-3-yl)ethyl]amino]ethyl]phenyl]-4-[4-[1-(2-phenyl)ethyl]thiazol-2-yl]benzenesulfonamide;
11. N-[4-[2-[[2-hydroxy-2-(pyridin-3-yl)ethyl]amino]ethyl]phenyl]-4-[4-(4-fluorophenyl)thiazol-2-yl]benzenesulfonamide;
12. N-[4-[2-[[2-hydroxy-2-(pyridin-3-yl)ethyl]amino]ethyl]phenyl]-4-[4-(2-naphthyl)thiazol-2-yl]benzenesulfonamide;
13. N-[4-[2-[[2-hydroxy-2-(pyridin-3-yl)ethyl]amino]ethyl]phenyl]-4-[4-(3,4,5-trifluorophenyl)thiazol-2-yl]benzenesulfonamide;
14. N-[4-[2-[[2-hydroxy-2-(pyridin-3-yl)ethyl]amino]ethyl]phenyl]-4-[4-(4-hexylphenyl)thiazol-2-yl]benzenesulfonamide;
15. N-[4-[2-[[2-hydroxy-2-(pyridin-3-yl)ethyl]amino]ethyl]phenyl]-4-[4-(trifluoromethoxy)phenylmethyl]thiazol-2-yl]benzenesulfonamide;
16. N-[4-[2-[[2-hydroxy-2-(pyridin-3-yl)ethyl]amino]ethyl]phenyl]-4-[4-(trifluoromethoxy)phenoxymethyl]thiazol-2-yl]benzenesulfonamide;
17. N-[4-[2-[[2-hydroxy-2-(pyridin-3-yl)ethyl]amino]ethyl]phenyl]-4-[4-(2-benzo[b]thienyl)thiazol-2-yl]benzenesulfonamide;
18. N-[4-[2-[[2-hydroxy-2-(pyridin-3-yl)ethyl]amino]ethyl]phenyl]-4-[4-(3-quinolinyl)thiazol-2-yl]benzenesulfonamide;
19. N-[4-[2-[[2-hydroxy-2-(pyridin-3-yl)ethyl]amino]ethyl]phenyl]-4-[4-(6-quinolinyl)thiazol-2-yl]benzenesulfonamide;
20. N-[4-[2-[[2-hydroxy-2-(pyridin-3-yl)ethyl]amino]ethyl]phenyl]-4-[4-(2-benzo[b]furyl)thiazol-2-yl]benzenesulfonamide;
21. N-[4-[2-[[2-hydroxy-2-(pyridin-3-yl)ethyl]amino]ethyl]phenyl]-4-[4-(3-indolyl)thiazol-2-yl]benzenesulfonamide;
22. N-[4-[2-[[2-hydroxy-2-(pyridin-3-yl)ethyl]amino]ethyl]phenyl]-4-[4-(2,4-difluorophenyl)thiazol-2-yl]benzenesulfonamide;
23. N-[4-[2-[[2-hydroxy-2-(pyridin-3-yl)ethyl]amino]ethyl]phenyl]-4-[4-(3,5-difluorophenyl)thiazol-2-yl]benzenesulfonamide;
24. N-[4-[2-[[2-hydroxy-2-(pyridin-3-yl)ethyl]amino]ethyl]phenyl]-4-[4-[4-(1,1-dimethylethyl)phenyl]thiazol-2-yl]benzenesulfonamide;
25. N-[4-[2-[[2-hydroxy-2-(pyridin-3-yl)ethyl]amino]ethyl]phenyl]-4-[4-(2,3-difluorophenyl)thiazol-2-yl]benzenesulfonamide;
26. N-[4-[2-[[2-hydroxy-2-(pyridin-3-yl)ethyl]amino]ethyl]phenyl]-4-[4-3-(trifluoromethyl)phenyl]thiazol-2-yl]benzenesulfonamide;
27. N-[4-[2-[[2-hydroxy-2-(pyridin-3-yl)ethyl]amino]ethyl]phenyl]-4-[4-(difluoromethyl)phenyl]thiazol-2-yl]benzenesulfonamide;
28. N-[4-[2-[[2-hydroxy-2-(pyridin-3-yl)ethyl]amino]ethyl]phenyl]-4-[4-(2,4-dichlorophenyl)thiazol-2-yl]benzenesulfonamide;
29. N-[4-[2-[[2-hydroxy-2-(pyridin-3-yl)ethyl]amino]ethyl]phenyl]-4-[4-[2-(trifluoromethyl)phenyl]thiazol-2-yl]benzenesulfonamide;
30. N-[4-[2-[[2-hydroxy-2-(pyridin-3-yl)ethyl]amino]ethyl]phenyl]-4-[4-[2-fluoro-4-(trifluoromethyl)phenyl]thiazol-2-yl]benzenesulfonamide;
31. N-[4-[2-[[2-hydroxy-2-(pyridin-3-yl)ethyl]amino]ethyl]phenyl]-4-[4-[4-fluoro-2-(trifluoromethyl)phenyl]thiazol-2-yl]benzenesulfonamide;
32. N-[4-[2-[[2-hydroxy-2-(pyridin-3-yl)ethyl]amino]ethyl]phenyl]-4-[4-[2,4-bis(trifluoromethyl)phenyl]thiazol-2-yl]benzenesulfonamide;
33. N-[4-[2-[[2-Hydroxy-2-(pyridin-3-yl)ethyl]amino]ethyl]phenyl]-4-[5-(4-fluorophenyl)thiazol-2-yl]benzenesulfonamide;
34. N-[4-[2-[[2-Hydroxy-2-(pyridin-3-yl)ethyl]amino]ethyl]phenyl]-4-[2-(4-trifluoromethylphenyl)thiazol-4-yl]benzenesulfonamide;
35. N-[4-[2-[[2-Hydroxy-2-(pyridin-3-yl)ethyl]amino]ethyl]phenyl]-4-[2-(4-trifluoromethylphenyl)thiazol-5-yl]benzenesulfonamide;
36. N-[4-[2-[[2-hydroxy-2-(pyridin-3-yl)ethyl]amino]ethyl]phenyl]-4-[4-(4-phenylphenyl)thiazol-2-yl]benzenesulfonamide;
37. N-[4-[2-[[2-hydroxy-2-(pyridin-3-yl)ethyl]amino]ethyl]phenyl]-4-[4-(3,4-dihydroxyphenyl)thiazol-2-yl]benzenesulfonamide;
38. N-[4-[2-[[2-hydroxy-2-(pyridin-3-yl)ethyl]amino]ethyl]phenyl]-4-[4-(4-hydroxyphenyl)thiazol-2-yl]benzenesulfonamide;
39. N-[4-[2-[[2-hydroxy-2-(pyridin-3-yl)ethyl]amino]ethyl]phenyl]-4-[4-(4-acetoxyphenyl)thiazol-2-yl]benzenesulfonamide;
40. N-[4-[2-[[2-hydroxy-2-(pyridin-3-yl)ethyl]amino]ethyl]phenyl]-4-[4-(4-acetamidophenyl)thiazol-2-yl]benzenesulfonamide;
41. N-[4-[2-[[2-hydroxy-2-(pyridin-3-yl)ethyl]amino]ethyl]phenyl]-4-[2-(4-trifluoromethoxyphenyl)thiazol-4-yl]benzenesulfonamide.

The compounds of the instant invention all have at least one asymmetric center as noted by the asterisk in structural Formula I. Additional asymmetric centers may be present on the molecule. Each such asymmetric center will produce two optical isomers and it is intended that all such optical isomers, as separated, pure or partially purified optical isomers or racemic mixtures thereof, be included within the ambit of the instant invention. In the case of the asymmetric center represented by the asterisk in Formula I, it has been found that the compound in which the hydroxy substituent is above the plane of the structure, as seen in Formula Ic, is more active and thus more preferred over the compound in which the hydroxy substituent is below the plane of the structure.

The following stereospecific structure represents the preferred stereoisomers of the instant invention:

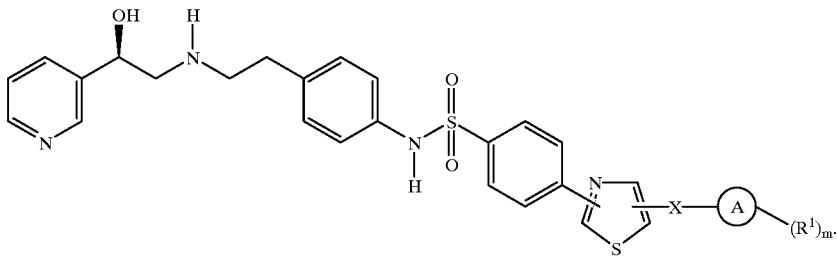

The thiazolyl moiety is numbered as follows:

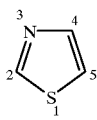

Throughout the instant application, the following terms have the indicated meanings:

"Alkylene" means —(CH$_2$)$_p$— where p is the designated carbon number; one or two of the hydrogen may be optionally replaced by methyl or halogen. Where the optionally substituted alkylene contains an oxygen, the oxygen may be at either end of the alkylene chain, or it may be embedded within the chain. Examples include OCH$_2$, CH$_2$O, CH$_2$OCH$_2$, C(CH$_3$)$_2$O, etc.

The alkyl groups specified above are intended to include those alkyl groups of the designated length in either a straight or branched configuration. Exemplary of such alkyl groups are methyl, ethyl, propyl, isopropyl, butyl, sec-butyl, tertiary butyl, pentyl, isopentyl, hexyl, isohexyl, and the like.

The alkoxy groups specified above are intended to include those alkoxy groups of the designated length in either a straight or branched configuration. Exemplary of such alkoxy groups are methoxy, ethoxy, propoxy, isopropoxy, butoxy, isobutoxy, tertiary butoxy, pentoxy, isopentoxy, hexoxy, isohexoxy and the like.

The term "halogen" is intended to include the halogen atoms fluorine, chlorine, bromine and iodine.

The term "carbocyclic ring" is intended to include both aromatic and nonaromatic rings containing only carbon atoms. Thus, a benzene ring fused to a C$_5$–C$_{10}$ carbocyclic ring, includes naphthyl, tetrahydronaphthyl, indanyl and indenyl. A 5 or 6-membered heterocyclic ring with from 1 to 4 heteroatoms selected from oxygen, sulfur and nitrogen fused to a C$_5$–C$_{10}$ carbocyclic ring includes benzene fused to a heterocyclic ring as well as a non-aromatic carbocyclic ring fused to a heterocyclic ring. The carbocyclic ring preferably is C$_5$–C$_7$.

A 5 and 6-membered heterocyclic ring, whether isolated or as a part of a fused ring system, is intended to include aromatic and unsaturated non-aromatic heterocycles; and where the heterocycle is part of a fused ring, at least one of the rings is aromatic. Examples of a 5 or 6-membered ring include pyridyl, pyrimidinyl, pyrrolyl, furyl, thienyl, imidazolyl, thiazolyl, thiadiazolyl, tetrazolyl, oxadiazolyl, oxazolyl, imidazolidinyl, pyrazolyl, isoxazolyl. Examples of a benzene ring fused to a 5 or 6-membered heterocyclic ring include benzothiadiazolyl, indolyl, indolinyl, benzodioxolyl, benzodioxanyl, benzothiophenyl, benzofuranyl, benzimidazolyl, benzoxazinyl, benzisoxazolyl, benzothiazolyl, 2,3-dihydrobenzofuranyl, quinolinyl, benzotriazolyl, benzoxazolyl, 1,2,3,4-tetrahydroisoquinolinyl, 1,2,3,4-tetrahydroquinolinyl. Examples of a 5 or 6-membered heterocyclic ring fused to a 5 or 6-membered heterocyclic ring include purinyl, furopyridine and thienopyridine. Examples of a 5 or 6-membered heterocyclic ring fused to a non-aromatic carbocyclic ring include tetrahydrobenzothiazolyl, 5,6,7,8-tetrahydroquinolinyl, 2,3-cyclopentenopyridyl, 4,5,6,7-tetrahydroindolyl, 5,6,7,8-tetrahydroisoquinolyl, 5,6,7,8-tetrahydroquinoxalinyl.

The term "composition", as in pharmaceutical composition, is intended to encompass a product comprising the active ingredient(s), and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of the present invention and a pharmaceutically acceptable carrier.

Throughout the instant application, when reference is made to "compounds of Formula I" it is meant to include, unless otherwise specified, pharmaceutically acceptable salts and prodrugs thereof. Prodrugs are derivatives of compounds of Formula I that are transformed in vivo to the active drug molecule; prodrugs include derivatives of free hydroxy, amino or carboxylic groups such as esters, ethers, amides, carbonates, carbamates, and N-alkyl derivatives. Specific examples of prodrugs of compounds of Formula I include: (a) derivation of the secondary amine such as N-alkylation (methyl, ethyl, isopropyl and 2-methoxyethyl), and N-acylation (1-pyrrolidinylacetyl, 4-morpholinylacetyl, (1-acetoxy)ethoxycarbonyl, and dimethylaminoacetyl); (b) derivation of the secondary hydroxy such as O-alkylation (ethyl) and O-acylation (acetyl, t-butoxycarbonyl, benzoyl, cyclopropylcarbonyl); and (c) the vicinally positioned secondary amine and secondary hydroxy taken together form a group of the formula

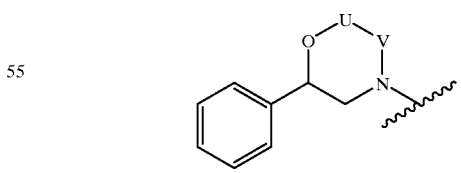

wherein U and V are independently a bond, carbonyl, methylene, CH(OH) or C(OH)(CH$_3$). Prodrugs of the above-described types may be readily prepared from compounds of Formula I using methods well know to persons skilled in the art.

Certain of the above defined terms may occur more than once in the above formula and upon such occurrence each term shall be defined independently of the other; thus for example, $NR^2R^2$ may represent $NH_2$, $NHCH_3$, $N(CH_3)CH_2CH_3$, and the like.

The compounds (I) of the present invention can be prepared as described in the following schemes. Thiazoles Ia, Ib and Ic are prepared via the Hantzsch thiazole synthesis (Sainsbury, M. In "Rodd's Chemistry of Carbon Compounds", Coffey, S., Ausell, M. F., Eds.; Elsevier: Amsterdam, 1986; Vol. IV C, 399–455) from the appropriate thioamide and 2-halocarbonyl derivative. As illustrated in aniline derivative 5 (Fisher, et. al., U.S. Pat. No. 5,561,142, Oct. 1, 1996) is treated with sulfonyl chloride 4, and a base such as pyridine in an anhydrous solvent such as dichloromethane or chloroform for 0.5 to 24 hours at temperatures of −20 to 50° C., preferably 0° C., followed by removal of the protecting group with, in the case of a tert-butylcarbamate, acid such as trifluoroacetic acid or methanolic hydrogen chloride, provides the thiazole Ia.

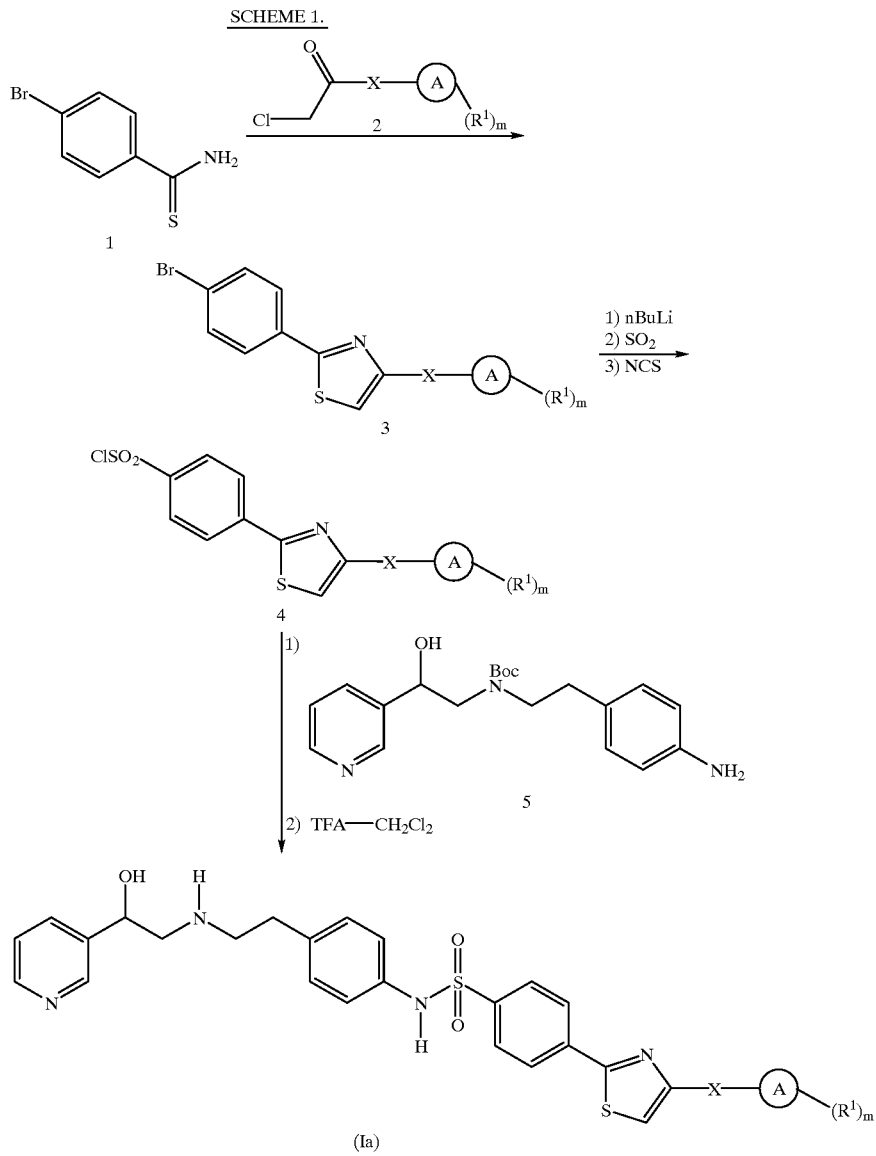

Scheme 1 for thiazoles Ia, 4-bromothiobenzamide (E. P. Papadopopoulos, *J. Org. Chem.* 1976, 41, 962) is condensed with the appropriate chloroketone 2, typically by heating in ethanol at reflux for 6 to 24 hours, to give bromophenylthiazole 3. Treatment with n-butyllithium, conveniently in tetrahydrofuran at −78° C., followed by sulfur dioxide, with warming to ambient temperature, provides the resultant lithium sulfinate. This may be readily converted to the corresponding sulfonyl chloride 4 by treatment with a chlorinating agent such as N-chlorosuccimide. The protected The chloroketones 2 are commercially available, known in the literature, or readily prepared by methods commonly known to those skilled in the art. Conveniently, the corresponding acid chloride 6 is treated with diazomethane followed by hydrogen chloride to provide chloroketone 2, as illustrated in Scheme 2.

SCHEME 2.

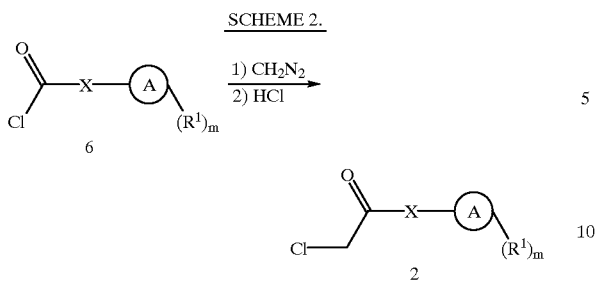

An alternate approach for the synthesis of thiazoles Ia is illustrated in Scheme 3. Nitrile 7 (Fisher, et. al., U.S. Pat. No. 5,561,142, Oct. 1, 1996) is converted to the corresponding thiamide by treatment with hydrogen sulfide in the presence of base such as triethylamine. The thiazole is formed from chloroketone 2 as described above. Removal of the t-butoxycarbonyl (Boc) protecting group by treatment with acid such as trifluoroacetic acid in dichloromethane or methanolic hydrogen chloride provides the desired thiazole (Ia).

Thiazoles Ib are prepared as illustrated in Scheme 4. Thioamide 8 is treated with the appropriate 2-bromoaldehyde 9 at elevated temperatures, conveniently in an inert solvent such as acetonitrile or acetonitrile/chloroform mixtures at reflux temperature, to provide, after deprotection as described above, thiazole Ib.

SCHEME 3.

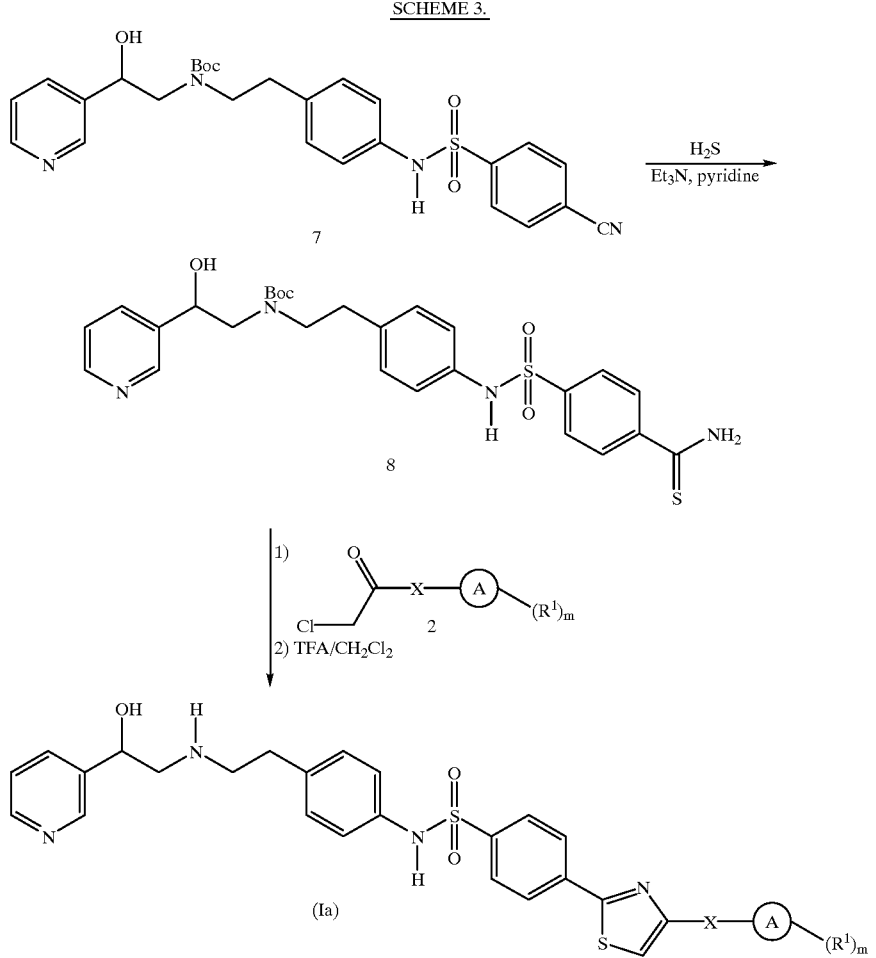

SCHEME 4.

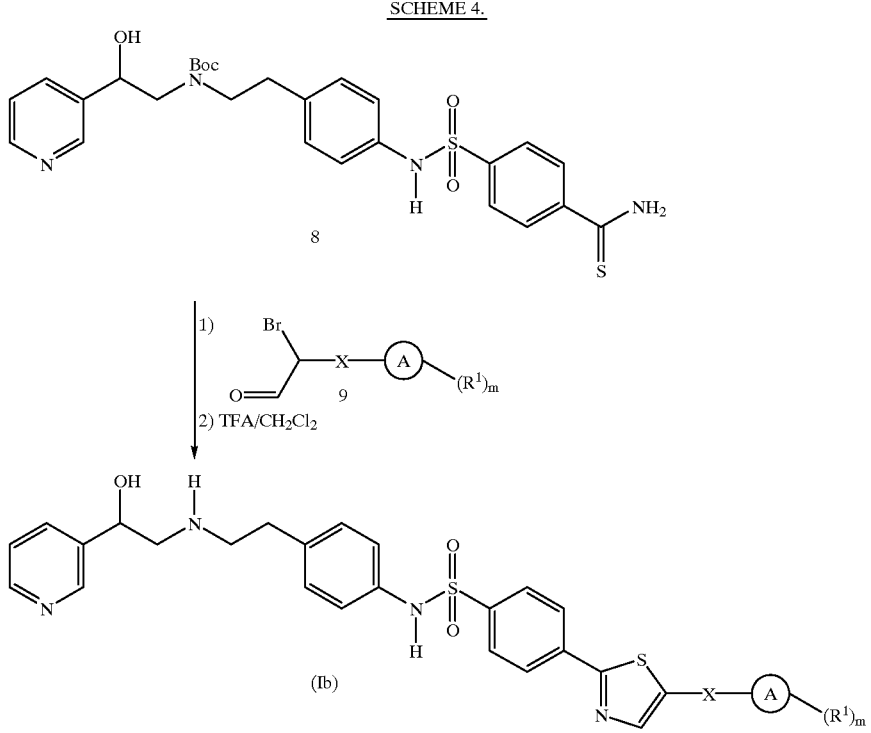

Bromoaldehydes 9 are known in the literature or readily prepared by methods comonly known to those skilled in the art. Conveniently, the corresponding alcohol 10 is oxidized to aldehyde 11, for example by treatment with o-iodoxybenzoic acid in DMSO (Frigerio and Santagostino, *Tetrahedron Lett.* 1994, 35, 8019). Bromination may be accomplished by treatment with a brominating agent, conveniently t-butyldimethylsilyl bromide/DMSO (Bellesia, et. al., *J. Chem. Research (S)* 1986, 428), to provide the desired bromoaldehydes 9.

SCHEME 5.

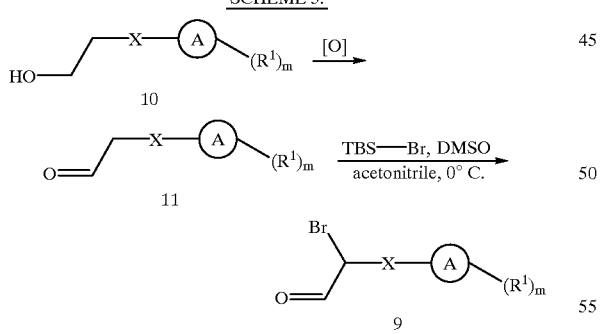

Thiazoles Ic are synthesized as outlined in Scheme 6. The appropriate nitrile 12, which is commercially available, known in the literature, or readily synthesized by methods known to those skilled in the art, is treated with hydrogen sulfide in the presence of a base such as triethylamine, and the resultant thioamide is treated with α,4-dibromoacetophenone (13) at elevated temperature, conveniently in refluxing ethanol, to provide thiazole 14. This compound is then protected at the 5-position, for example as the 5-trimethylsilyl derivative by treatment with n-butyllithium followed by trimethylsilyl chloride. Conversion of the resultant bromo derivative 15 to the corresponding sulfonyl chloride followed by sulfonamide formation with aniline 5 and removal of the Boc protecting group with TFA occurs as described above for Scheme 1. The silyl group is then removed, conveniently by treatment with hydrogen fluoride in acetonitrile, to provide the desired thiazole Ic.

SCHEME 6.

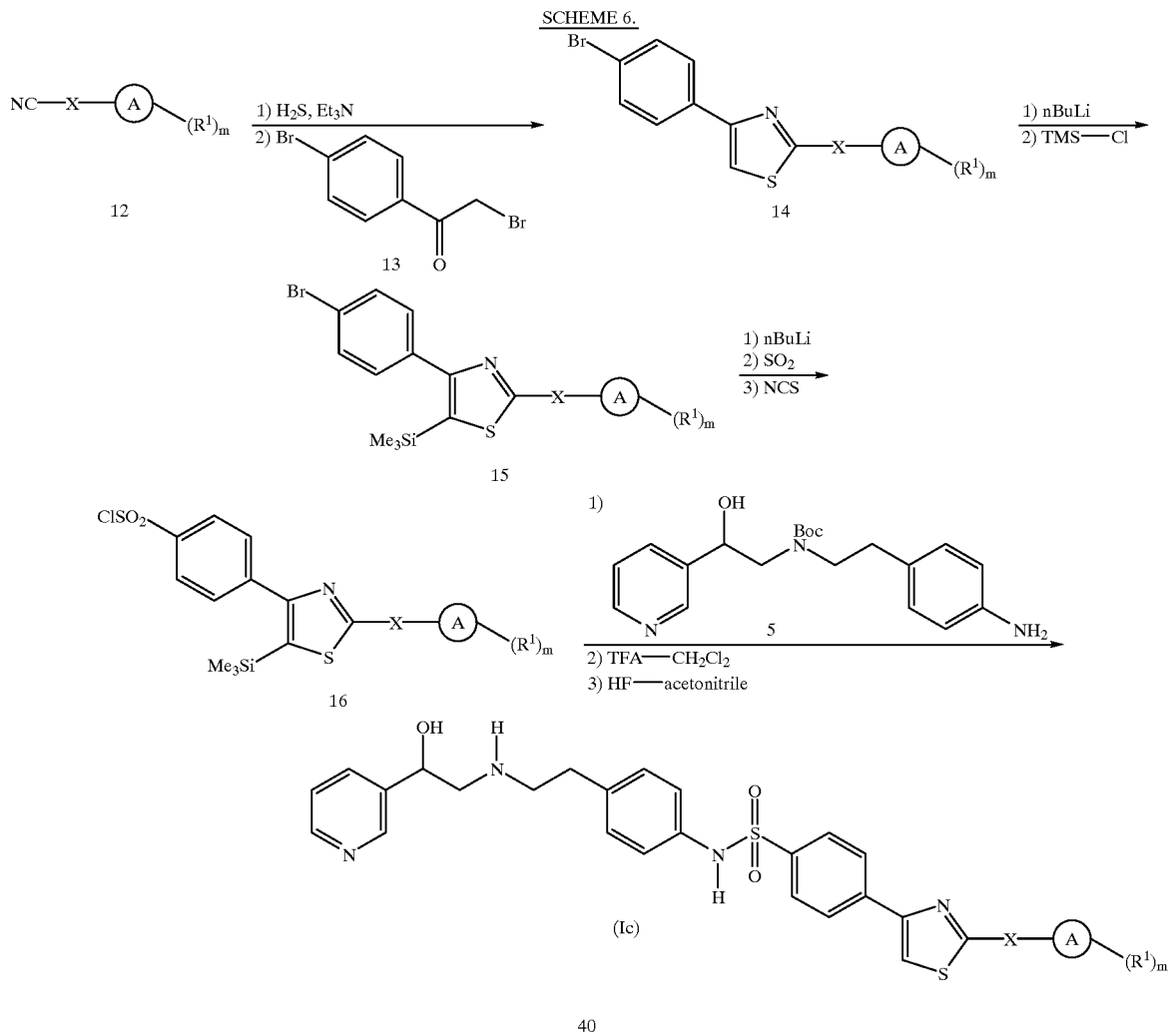

Thiazoles Id may be prepared as illustrated in Scheme 7. Aminoacetophenone 18 is prepared from bromo derivative 13 using a modified Delepine reaction (Goddard, C. J. *J. Heterocyclic Chem.* 1991, 28, 17), by treatment of compound 13 with hexamethylenetetramine 17 followed by hydrochloric acid in methanol. Amine 18 is then treated with the appropriate acid chloride to give ketone 20. Formation of the thiazole is accomplished by treatment with Lawesson's reagent at elevated temperature, conveniently in refluxing toluene. The resultant bromo derivative 21 is converted to the desired thiazole Id as described above in Scheme 1 for thiazole Ia.

Acid chlorides 19 are commercially available, known in the literature, or readily prepared using methods commonly known to those skilled in the art.

SCHEME 7.

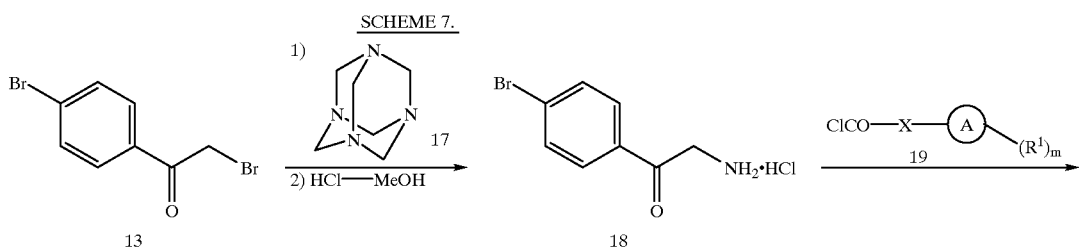

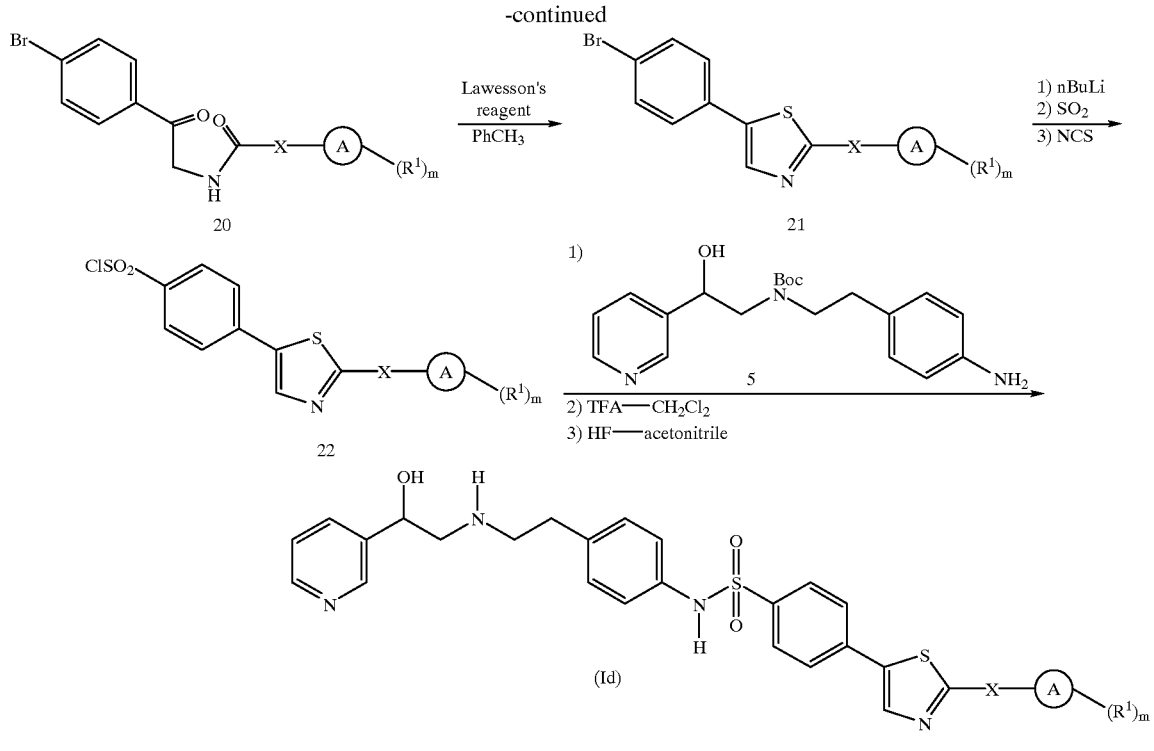

In some cases, the product I from the reactions described in Schemes 1–7 may be further modified, for example, by the removal of protecting groups or the manipulation of substituents on $R^1$. These manipulations may include, but are not limited to, reduction, oxidation, alkylation, acylation, and hydrolysis reactions which are commonly known to those skilled in the art.

Compounds of Formula I contain one or more asymmetric centers and can thus occur as racemates and racemic mixtures, single enantiomers, diastereomeric mixtures and individual diastereomers. The present invention is meant to comprehend all such isomeric forms of the compounds of Formula I.

Some of the compounds described herein contain olefinic double bonds, and unless specified otherwise, are meant to include both E and Z geometric isomers.

Some of the compounds described herein may exist as tautomers such as keto-enol tautomers. The individual tautomers as well as mixture thereof are encompassed with compounds of Formula I.

Compounds of the Formula I may be separated into diastereoisomeric pairs of enantiomers by, for example, fractional crystallization from a suitable solvent, for example methanol or ethyl acetate or a mixture thereof. The pair of enantiomers thus obtained may be separated into individual stereoisomers by conventional means, for example by the use of an optically active acid as a resolving agent.

Alternatively, any enantiomer of a compound of the general Formula I or Ia may be obtained by stereospecific synthesis using optically pure starting materials of known configuration.

The term "pharmaceutically acceptable salts" refers to salts prepared from pharmaceutically acceptable non-toxic bases or acids including inorganic or organic bases and inorganic or organic acids. Salts derived from inorganic bases include aluminum, ammonium, calcium, copper, ferric, ferrous, lithium, magnesium, manganic salts, manganous, potassium, sodium, zinc, and the like. Particularly preferred are the ammonium, calcium, magnesium, potassium, and sodium salts. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylenediamine, diethylamine, 2-diethylaminoethanol, 2-dimethylaminoethanol, ethanolamine, ethylenediamine, N-ethyl-morpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like.

When the compound of the present invention is basic, salts may be prepared from pharmaceutically acceptable non-toxic acids, including inorganic and organic acids. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid, and the like.

Compounds of the present invention are potent agonists of the β3-adrenoceptor, and as such are useful in treating or preventing diseases, disorders or conditions mediated by the activation of β3-adrenoceptor. Thus one aspect of the present invention provides a method for the treatment, control or prevention of such diseases, disorders, or conditions in a mammal which comprises administering to such mammal a therapeutically effective amount of a compound of Formula I. The term "mammal" includes human and non-human animals such as dogs and cats and the like. The diseases, disorders or conditions for which compounds of the present invention are useful in treating or preventing include, but are not limited to, (1) diabetes mellitus, (2) hyperglycemia, (3) obesity, (4) hyperlipidemia, (5) hypertriglyceridemia, (6) hypercholesterolemia, (7) atherosclerosis of coronary, cerebrovascular and peripheral arteries, (8) gastrointestinal disorders including peptid ulcer, esophagitis, gastritis and duodenitis, (including that induced by *H. pylori*), intestinal ulcerations (including inflammatory bowel disease, ulcerative colitis, Crohn's disease and proctitis) and gastrointestinal ulcerations, (9) neurogenic inflammation of airways, including cough, asthma, (10) depression, (11) prostate diseases such as benign prostate hyperplasia, (12) irritable bowel syndrome and other disorders needing decreased gut motility, and (13) elevated intraocular pressure and glaucoma.

Any suitable route of administration may be employed for providing a mammal, especially a human with an effective dosage of a compound of the present invention. For example, oral, rectal, topical, parenteral, ocular, pulmonary, nasal, and the like may be employed. Dosage forms include tablets, troches, dispersions, suspensions, solutions, capsules, creams, ointments, aerosols, and the like. Preferably compounds of Formula I are administered orally.

The effective dosage of active ingredient employed may vary depending on the particular compound employed, the mode of administration, the species of mammals being treated, the condition being treated and the severity of the condition being treated. Such dosage may be ascertained readily by a person skilled in the art of human or veterinary medicine.

When treating obesity (in conjunction with diabetes and/or hyperglycemia, or alone) in human or non-human animals such as dogs and cats, generally satisfactory results are obtained when the compounds of the present invention are administered at a daily dosage of from 0.01 milligram to about 100 milligrams per kilogram of animal body weight, preferably given in a single dose or in divided doses two to six times a day, or in sustained release form. In the case of a 70 kg adult human, the total daily dose will generally be from about 0.7 milligrams to about 3500 milligrams. This dosage regimen may be adjusted to provide the optimal therapeutic response.

When treating diabetes mellitus and/or hyperglycemia, as well as other diseases or disorders for which compounds of formula I are useful, generally satisfactory results are obtained when the compounds of the present invention are administered at a daily dosage of from about 0.001 milligram to about 100 milligram per kilogram of animal body weight, preferably given in a single dose or in divided doses two to six times a day, or in sustained release form. In the case of a 70 kg adult human, the total daily dose will generally be from about 0.07 milligrams to about 350 milligrams. This dosage regimen may be adjusted to provide the optimal therapeutic response.

Another aspect of the present invention provides pharmaceutical compositions which comprises a compound of Formula I and a pharmaceutically acceptable carrier. The pharmaceutical compositions of the present invention comprise a compound of Formula I as an active ingredient or a pharmaceutically acceptable salt thereof, and may also contain a pharmaceutically acceptable carrier and optionally other therapeutic ingredients. The term "pharmaceutically acceptable salts" refers to salts prepared from pharmaceutically acceptable non-toxic bases or acids including inorganic bases or acids and organic bases or acids.

The compositions include compositions suitable for oral, rectal, topical, parenteral (including subcutaneous, intramuscular, and intravenous), ocular (ophthalmic), pulmonary (nasal or buccal inhalation), or nasal administration, although the most suitable route in any given case will depend on the nature and severity of the conditions being treated and on the nature of the active ingredient. They may be conveniently presented in unit dosage form and prepared by any of the methods well-known in the art of pharmacy.

In practical use, the compounds of Formula I can be combined as the active ingredient in intimate admixture with a pharmaceutical carrier according to conventional pharmaceutical compounding techniques. The carrier may take a wide variety of forms depending on the form of preparation desired for administration, e.g., oral or parenteral (including intravenous). In preparing the compositions for oral dosage form, any of the usual pharmaceutical media may be employed, such as, for example, water, glycols, oils, alcohols, flavoring agents, preservatives, coloring agents and the like in the case of oral liquid preparations, such as, for example, suspensions, elixirs and solutions; or carriers such as starches, sugars, microcrystalline cellulose, diluents, granulating agents, lubricants, binders, disintegrating agents and the like in the case of oral solid preparations such as, for example, powders, hard and soft capsules and tablets, with the solid oral preparations being preferred over the liquid preparations.

Because of their ease of administration, tablets and capsules represent the most advantageous oral dosage unit form in which case solid pharmaceutical carriers are obviously employed. If desired, tablets may be coated by standard aqueous or nonaqueous techniques. Such compositions and preparations should contain at least 0.1 percent of active compound. The percentage of active compound in these compositions may, of course, be varied and may conveniently be between about 2 percent to about 60 percent of the weight of the unit. The amount of active compound in such therapeutically useful compositions is such that an effective dosage will be obtained. The active compounds can also be administered intranasally as, for example, liquid drops or spray.

The tablets, pills, capsules, and the like may also contain a binder such as gum tragacanth, acacia, corn starch or gelatin; excipients such as dicalcium phosphate; a disintegrating agent such as corn starch, potato starch, alginic acid; a lubricant such as magnesium stearate; and a sweetening agent such as sucrose, lactose or saccharin. When a dosage unit form is a capsule, it may contain, in addition to materials of the above type, a liquid carrier such as a fatty oil.

Various other materials may be present as coatings or to modify the physical form of the dosage unit. For instance, tablets may be coated with shellac, sugar or both. A syrup or elixir may contain, in addition to the active ingredient, sucrose as a sweetening agent, methyl and propylparabens as preservatives, a dye and a flavoring such as cherry or orange flavor.

Compounds of formula I may also be administered parenterally. Solutions or suspensions of these active compounds can be prepared in water suitably mixed with a surfactant such as hydroxy-propylcellulose. Dispersions can also be prepared in glycerol, liquid polyethylene glycols and mixtures thereof in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (e.g. glycerol, propylene glycol and liquid polyethylene glycol), suitable mixtures thereof, and vegetable oils.

Compounds of Formula I may be used in combination with other drugs that are used in the treatment/prevention/ suppression or amelioration of the diseases or conditions for which compounds of Formula I are useful. Such other drugs may be administered, by a route and in an amount commonly used therefor, contemporaneously or sequentially with a compound of Formula I. When a compound of Formula I is used contemporaneously with one or more other drugs, a pharmaceutical composition containing such other drugs in addition to the compound of Formula I is preferred. Accordingly, the pharmaceutical compositions of the present invention include those that also contain one or more other active ingredients, in addition to a compound of Formula I. Examples of other active ingredients that may be combined with a compound of Formula I, either administered separately or in the same pharmaceutical compositions, include, but are not limited to:

(a) insulin sensitizers including (i) PPARγ agonists such as the glitazones (e.g. troglitazone, pioglitazone, englitazone, MCC-555, BRL49653 and the like), and compounds disclosed in WO97/27857, 97/28115, 97/28137 and 97/27847; (ii) biguanides such as metformin and phenformin;

(b) insulin or insulin mimetics;

(c) sulfonylureas such as tolbutamide and glipizide;

(d) α-glucosidase inhibitors (such as acarbose), (e) cholesterol lowering agents such as (i) HMG-CoA reductase inhibitors (lovastatin, simvastatin and pravastatin, fluvastatin, atorvastatin, and other statins), (ii) sequestrants (cholestyramine, colestipol and a dialkylaminoalkyl derivatives of a cross-linked dextran), (ii) nicotinyl alcohol nicotinic acid or a salt thereof, (iii) proliferator-activater receptor α agonists such as fenofibric acid derivatives (gemfibrozil, clofibrat, fenofibrate and benzafibrate), (iv) inhibitors of cholesterol absorption for example beta-sitosterol and (acyl CoA:cholesterol acyltransferase) inhibitors for example melinamide, (v) probucol, (vi) vitamin E, and (vii) thyromimetics;

(f) PPARδ agonists such as those disclosed in WO97/28149;

(g) antiobesity compounds such as fenfluramine, dexfenfluramine, phentermine, sibutramine, orlistat, and other $\beta_3$ adrenergic receptor agonists;

(h) feeding behavior modifying agents such as neuropeptide Y antagonists (e.g. neuropeptide Y5) such as those disclosed in WO 97/19682, WO 97/20820, WO 97/20821, WO 97/20822 and WO 97/20823;

(i) PPARα agonists such as described in WO 97/36579 by Glaxo;

(j) PPARγ antagonists as described in WO97/10813; and (k) serotonin reuptake inhibitors such as fluoxetine and sertraline The following in vitro assays are suitable for screening compounds for β3 agonist activity and for determining selectivity for the β3 receptor over the β1/β2 receptors:

Functional Assay: cAMP production in response to ligand is measured according to Barton et al (1991, Agonist-induced desensitization of D2 dopamine receptors in human Y-79 retinoblastoma cells. Mol. Pharmacol. v3229:650–658) modified as follows. Chinese hamster ovary (CHO) cells, stably transfected with the cloned β-adrenergic receptor ($\beta_1$, $\beta_2$ or $\beta_3$) are harvested after 3 days of subculturing. Harvesting is done with Enzyme-free Dissociation Media (Specialty Media). Cells are counted and distributed in the assay tubes, after being resuspended in Tris buffer (ACC buffer: 75 mM Tris, pH 7.4, 250 mM Sucrose, 12.5 mM $MgCl_2$, 1.5 mM EDTA, 0.2 mM Sodium Metabisulfite, 0.6 mM IBMX) containing an antioxidant and a phosphodiesterase inhibitor. Reaction is initiated by mixing 200,000 cells in 100 μL with 20 μL of a 6× stock of ligand/unknown to be tested. Tubes shake at 275 rpm for 45 min at room temperature. The reaction is stopped by boiling the tubes for 3 min. The cell lysate is diluted 5-fold in 0.1 N HCl and then acetylated by the mixture of 150 μL of acid-diluted sample with 6 μL of acetylation mixture (acetic anhydride/triethylamine, 1:2.5). The cAMP produced in response to the ligand is measured in the lysate by competing against $^{125}$I-cAMP for binding to a $^{125}$I-cAMP-directed antibody using an automated RIA machine (ATTOFLO, Atto Instruments, Baltimore, Md., Brooker et al 1979, Radioimmunoassay of Cyclic AMP and Cyclic GMP. Advances in Cyclic Nucleotide Research. vol 10: 1–32.). The unknown cAMP level is determined by comparing levels to a standard curve. Alternatively, cAMP is measured using the cAMP SPA kit (code number RPA 556) from Amersham according to the manufacturer's instructions. Samples tested with the latter method do not need to be acetylated.

The non-selective, full agonist β-adrenergic ligand isoproterenol is used at all three receptors to determine maximal stimulation. The human β3 adrenergic receptor (AR) selective ligand (S)-N-[4-[2-[[2-hydroxy-3-(4-hydroxyphenoxy)propyl]amino]ethyl]phenyl]-4-iodobenzenesulfonamide is used as a control in all assays. Isoproterenol is titrated at a final concentration in the assay of $10^{-10}$ M to $10^{-5}$ M for the β3 AR and $10^{-11}$ M to $10^{-6}$ M for the β1 AR and β2 AR assays. (S)-N-[4-[2-[[2-Hydroxy-3-(4-hydroxyphenoxy)propyl]amino]ethyl]-phenyl]-4-iodobenzenesulfonamide is titrated at the β3 receptor at concentration of $10^{-11}$ M to $10^{-6}$ M. At the β31 AR the concentrations used are $10^{-8}$ M, $10^{-7}$ M, $3 \times 10^{-7}$ M, $10^{-6}$ M, $3 \times 10^{-6}$ M and $10^{-5}$ M. For the β2 AR a single concentration of $10^{-5}$ M is used.

Unknown ligands are initially tested at the β3 AR at a final concentration in the assay of $10^{-7}$ M. Compounds that have an activation at this concentration equal to or greater than 35% of the isoproterenol stimulation are titrated at the β3 AR at concentrations equal to those used to titrate the control (S)-N-[4-[2-[[2-hydroxy-3-(4-hydroxyphenoxy)propyl] amino]ethyl]phenyl]-4-iodobenzenesulfonamide to determine the $EC_{50}$. The $EC_{50}$ is defined as the concentration of compound that gives 50% activation of its own maximum. Data are analyzed using the Prism program (GraphPan, San Diego, Calif.).

Binding Assay: Compounds are also assayed at the β1 and β2 receptors to determine selectivity. This is done for all compounds using a 6 point binding assay as follows: CHO cells expressing the β1 and the β2 receptors are grown for 3–4 days after splitting. The attached cells are washed with PBS and lysed in 1 mM Tris, pH 7.2 for 10 minutes in ice. The flasks are scraped and the membranes centrifuged at 38,000×g for 15 minutes at 4° C. The membranes are resuspended in TME buffer (75 mM Tris, pH 7.4, 12.5 mM $MgCl_2$, 1.5 mM EDTA) at a concentration of 1 mg protein/ ml. Large batches of membranes can be prepared, aliquoted and stored at −70° C. for up to a year without loss of potency. The binding assay is performed by incubating together membranes (20–50 μg of protein), the radiolabelled tracer $^{125}$I-cyanopindolol ($^{125}$I-CYP, 45 pM), and the test compounds at final concentrations ranging from $10^{-10}$ M to $10^{-5}$ M in a final volume of 250 μL of TME buffer. The tubes are incubated for 1 hour with shaking at room temperature and the samples are filtered in an IMSCO 96-well cell harvester. The filters are counted in a Gamma counter and the data are analyzed using a 4 parameter fit routine in RS1 (program developed in house using well documented statistical analysis programs) to determine the $IC_{50}$. The $IC_{50}$ is defined as the concentration of the compound capable of inhibiting 50% of the binding of the radiolabelled tracer ($^{125}$I-CYP). A compound's selectivity for the β3 receptor may be determined by calculating the ratio ($IC_{50}$ β1 AR, β2 AR)/($EC_{50}$ β3 AR).

The following examples are provided so that the invention might be more fully understood. They should not be construed as limiting the invention in any way.

EXAMPLE 1

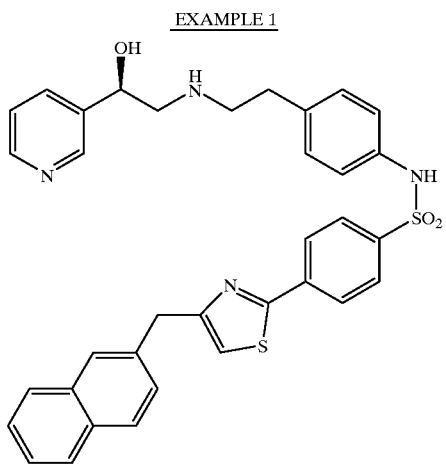

(R)-N-[4-[2-[[2-Hydroxy-2-(pyridin-3-yl)ethyl]amino]ethyl]phenyl]-4-[4-(2-naphthylmethyl)thiazol-2-yl]benzenesulfonamide Step A. 2-Naphthylmethyl chloromethyl ketone A mixture of 2-naphthylacetic acid (0.75 g) and 5 mL of thionyl chloride was warmed at reflux for 1 h. Excess thionyl chloride was removed under reduced pressure, followed by azeotropic distillation with two portions of benzene. The residual yellow liquid was dissolved in 10 mL of dry ether and was added dropwise to an ice-cold solution of excess diazomethane etherate (generated from Diazald and aqueous potassium hydroxide at 0° C.). The reaction mixture was stirred at 0° C. for 1 h, and was then concentrated under reduced pressure. The yellow oily residue was dissolved in 40 mL of dry ether, cooled in ice, and a solution of hydrochloric acid in methanol (prepared from 0.30 mL of acetyl chloride and 2.0 mL of methanol at 0° C.) was added dropwise. After 1 h, the solution was concentrated under reduced pressure. The waxy solid residue was recrystallized from hexane, affording 0.81 g of the title compound, mp 78–79° C.: $^1$H NMR (400 MHz, CDCl$_3$) δ 7.80 (m, 3H), 7.68 (s, 1H), 7.47 (m, 2H), 7.31 (dd, J=8.4 and 1.8 Hz, 1H), 4.13 (s, 2H), 4.04 (s, 2H).

Step B. 2-(4-Bromophenyl)-4-(2-naphthylmethyl)thiazole

A solution of 0.50 g of 4-bromothiobenzamide (E. P. Papadopoulos, J. Org. Chem. 1976, 41, 962) and 0.44 g of 2-naphthylmethyl chloromethyl ketone obtained above in 10 mL of absolute ethanol was warmed at reflux for 18 h. The mixture was cooled in ice, and the solid was collected and washed with cold ethanol to afford 0.53 g of tan powder, mp 136–138° C.: $^1$H NMR (400 MHz, CDCl$_3$) δ 7.85 (d, J=8.6 Hz, 2H), 7.74–7.84 (m, 4H), 7.67 (d, J=8.6 Hz, 2H), 7.44 (m, 3H), 7.28 (s, 1H), 4.40 (s, 2H).

Step C. 4-[4-(2-Naphthylmethyl)thiazol-2-yl]benzenesulfonyl chloride

A solution of the above aryl bromide (0.53 g) in 10 mL of dry tetrahydrofuran was cooled to −78° C., and a solution of n-butyllithium (1.0 mL of 1.6 M in hexanes) was added dropwise. After 30 min, a steady stream of sulfur dioxide was introduced into the surface of the deep brown-red solution for a period of 5 min. The resulting yellow solution was stirred at −78° C. for 10 min, and was then allowed to warm to room temperature. After 1 h, the mixture was concentrated under reduced pressure, and the residue was stirred with 20 mL of a 1:1 mixture of ether:hexane. The supernatant was decanted off, and the resulting off-white powder was dried under reduced pressure, and was subsequently suspended in 10 mL of dichloromethane and cooled in an ice-bath. N-chlorosuccinimide (0.175 g) was added in one portion, and the mixture was stirred at 0° C. for 15 min. The cooling bath was removed and, after 30 min, the mixture was diluted with dichloromethane and filtered through a short pad of Celite. The residue obtained after evaporation was purified by flash chromatography on a silica gel column (8% ethyl acetate/hexane), affording 0.042 g of the title compound as an off-white solid: $^1$H NMR (400 MHz, CDCl$_3$) δ 7.93 (d, J=8.5 Hz, 2H), 7.70–7.85 (m, 4H), 7.67 (d, J=8.5 Hz, 2H), 7.40 (m, 3H), 7.26 (s, 1H), 4.43 (s, 2H).

Step D. (R)-N-[4-[2-[[2-Hydroxy-2-(pyridin-3-yl)ethyl]amino]ethyl]phenyl]-4-[4-(2-naphthylmethyl)thiazol-2-yl]benzenesulfonamide A solution of 0.035 g of (R)-N-[2-[4-(aminophenyl)]ethyl]-2-hydroxy-2-(pyrid-3-yl)ethylcarbamic acid 1,1-dimethylethyl ester (Fisher, et. al., U.S. Pat. No. 5,561,142, Oct. 1, 1996) in 1.5 mL of dichloromethane was treated with the above sulfonyl chloride (0.042 g) and pyridine (0.015 mL). The solution was stirred at 25° C. for 18 h, and trifluoroacetic acid (3 mL) was added. After stirring for 1.5 h, the solution was concentrated under reduced pressure. Azeotropic distillation with methanol (10 mL) left an orange, viscous oil, which was purified by flash chromatography on silica gel (9:1 dichloromethane:10% ammonium hydroxide/methanol eluant) to afford 0.083 g of the title compound as a yellow foam. $^1$H NMR (400 MHz, CD$_3$OD) δ 8.50 (d, J=2.0 Hz, 1H), 8.41 (dd, J=4.9 and 1.6 Hz, 1H), 7.83 (d, J=8.0 Hz, 2H), 7.64–7.80 (m, 4H), 7.58 (s, 1H), 7.3–7.5 (m, 7H), 7.04 (two overlapping d, J=8.6 Hz, 4H), 4.79 (dd, J=7.3 and 5.7 Hz, 1H), 4.36 (s, 2H), 2.4–2.9 (m, 6H). FAB MS m/z 621.

EXAMPLE 2

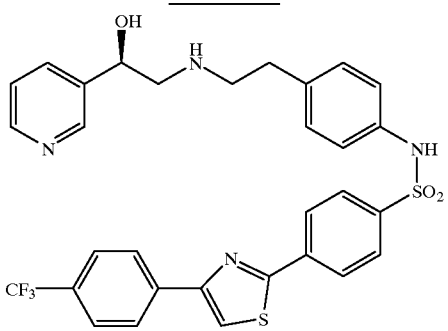

(R)-N-[4-[2-[[2-Hydroxy-2-(pyridin-3-yl)ethyl]amino]ethyl]phenyl]-4-[4-(4-trifluoromethylphenyl)thiazol-2-yl]benzenesulfonamide and salts Step A. (R)-N-[4-[2-[N-(1,1-Dimethylethoxycarbonyl)-N-[2-hydroxy-2-(pyridin-3-yl)ethyl]amino]ethyl]phenyl]-4-aminothiocarbonyl)benzene sulfonamide A steady stream of hydrogen sulfide was bubbled into a solution of 10.2 g of (R)-N-[4-[2-[N-(1,1-dimethylethoxycarbonyl)-N-[2-hydroxy-2-(pyridin-3-yl)ethyl]amino]ethyl]phenyl]-4-cyanobenzenesulfonamide (Fisher, et. al., U.S. Pat. No. 5,561,142, Oct. 1, 1996) and triethylamine (2.9 mL) in 100 mL of pyridine at 25° C. for 15 min. The green solution was stirred for 2.5 h, and then nitrogen was bubbled through the solution for 30 min. The reaction mixture was concentrated under reduced pressure, and the residue was purified by flash chromatography on silica gel (8% -methanol in dichloromethane eluant), affording 9.31 g of title compound as a bright yellow foam. $^1$H NMR (400 MHz, CD$_3$OD) δ 8.45 (m, 2H), 7.87 (d, J=8.5 Hz, 2H), 7.80 (m, 1H), 7.70 (m, 2H), 7.01 (overlapping s, 4H and m, 1H), 4.84 (m, 1H), 3.15–3.45 (m, 4H), 2.7 (m, 2H), 1.30 (s, 9H).

Step B. (R)-N-[4-[2-[[2-Hydroxy-2-(pyridin-3-yl)ethyl]amino]ethyl]phenyl]-4-[4-(4-trifluoromethylphenyl)thiazol-2-yl]benzenesulfonamide A mixture of 1.77 g of thioamide from step A above and 1.02 g of 4-(trifluoromethyl)phenyl chloromethylketone (synthesized from 4-(trifluoromethyl)benzoyl chloride and diazomethane as described in Example 1, Step A) in absolute ethanol (10 mL) was warmed at reflux for 18 h. The cooled reaction mixture was concentrated under reduced pressure, and the residue was dissolved in 8 mL of dichloromethane and 2 mL of trifluoroacetic acid (TFA). After stirring for 1 h at ambient temperature, the solution was concentrated under reduced pressure. Residual TFA was removed by azeotropic distillation with dichloromethane, and the residue was purified by flash chromatography (9:1 dichloromethane/10% NH$_4$OH in methanol eluant), affording the title compound (1.36 g) as a white powder. $^1$H NMR (400 MHz, CD$_3$OD) δ 8.49 (d, J=2.1 Hz, 1H), 8.40 (dd, J=5.0 and 1.5 Hz, 1H), 8.18 (d, J=7.9 Hz, 2H), 8.12 (d, J=8.6 Hz, 2H), 8.09 (s, 1H), 7.82 (d, J=8.6 Hz, 2H), 7.77 (m, 1H), 7.71 (d, J=8.6 Hz, 2H), 7.35 (dd, J=7.9 and 5.0 Hz, 1H), 7.09 (d, J=8.6 Hz, 2H), 7.04 (d, J=8.6 Hz, 2H), 4.80 (dd, J=7.3 and 5.7 Hz, 1H), 2.70–2.90 (m, 6H). FAB MS m/z 625.

Dihydrochloride Salt of Title Compound

The free base from step B above (2.50 g) was briefly stirred with a methanolic solution of hydrochloric acid (prepared by addition of 0.64 mL of acetyl chloride to 10 mL of methanol at 0° C. for 15 min). Concentration under reduced pressure and drying in vacuo left 2.81 g of a light yellow powder, which was dissolved in 35 mL of absolute ethanol, filtered, seeded and allowed to slowly evaporate at ambient temperature. The resulting crystalline solid was collected, washed with cold ethanol, and dried in vacuo to afford the title compound (2.60 g), mp 215–218° C. $^1$H NMR (400 MHz, CD$_3$OD) δ 8.96 (s, 1H), 8.82 (d, J=5.8 Hz, 1H ), 8.68 (d, J=8.2 Hz, 1H), 8.20 (d, J=8.2 Hz, 2H), 8.14 (d, J=8.6 Hz, 2H), 8.13 (s, 1H), 8.08 (dd, J=8.0 and 5.7 Hz, 1H), 7.87 (d, J=8.6 Hz, 2H), 7.73 (d, J=8.0 Hz, 2H), 7.20 (d, J=8.6 Hz, 2H), 7.13 (d, J=8.6 Hz, 2H), 5.30 (dd, J=10.0 and 2.9 Hz, 1H), 3.44 (dd, J=12.7 and 2.9 Hz, 1H), 3.20–3.35 (m, 4H), 2.97 (t, J=8.3 Hz, 2H). FAB MS m/z 625 (M+1).

Dihydrobromide Salt of Title Compound

The free base in methanol was treated with 2.2 equivalents of methanolic hydrogen bromide solution, stirred for 30 min at room temperature, filtered, and the filtrate concentrated and dried under reduced pressure. The residual powder was suspended in 2-propanol and warmed at reflux for 18 h. The solution was cooled slowly to room temperature with stirring, and was subsequently cooled in an ice-water bath. The pale yellow, crystalline powder was collected, washed with cold 2-propanol and dried in vacuo to afford the title compound, mp 199–202° C. $^1$H NMR (400 MHz, CD$_3$OD) δ 8.97 (s, 1H), 8.82 (d, J=5.4 Hz, 1H), 8.68 (d, J=8.2 Hz, 1H), 8.20 (d, J=8.0 Hz, 2H), 8.14 (d, J=8.6 Hz, 2H), 8.13 (s, 1H), 8.08 (dd, J=8.0 and 5.7 Hz, 1H), 7.86 (d, J=8.6 Hz, 2H), 7.73 (d, J=8.0 Hz, 2H), 7.20 (d, J=8.6 Hz, 2H), 7.13 (d, J=8.6 Hz, 2H), 5.31 (dd, J=10.0 and 3.1 Hz, 1H), 3.44 (dd, J=12.8 and 3.1 Hz, 1H), 3.20–3.35 (m, 4H), 2.98 (t, J=8.3 Hz, 2H).

Dimaleate Salt of Title Compound

The free base was suspended in 2-propanol and treated with 2.0 equivalents of maleic acid. The suspension was warmed at reflux until all solids were dissolved, filtered, allowed to cool slightly, seeded and then allowed to stand at room temperature overnight. The precipitated solid was collected, washed with 2-propanol, and dried in vacuo to afford the title compound as an off-white, crystalline powder, mp 154–156° C. $^1$H NMR (400 MHz, CD$_3$OD) δ 8.60 (d, J=2.4 Hz, 1H), 8.51 (dd, J=4.9 and 1.6 Hz, 1H), 8.20 (d, J=7.9 Hz, 2H), 8.14 (d, J=8.5 Hz, 2H), 8.13 (s, 1H), 7.93 (m, 1H), 7.86 (d, J=8.6 Hz, 2H), 7.49 (dd, J=7.8 and 4.7 Hz, 1H), 7.17 (d, J=8.6 Hz, 2H), 7.12 (d, J=8.6 Hz, 2H), 6.27 (4 H, s, maleic acid), 5.02 (dd, J=10.1 and 3.3 Hz, 1H), 3.15–3.35 (m, 4H), 2.95 (m, 2H).

EXAMPLE 3

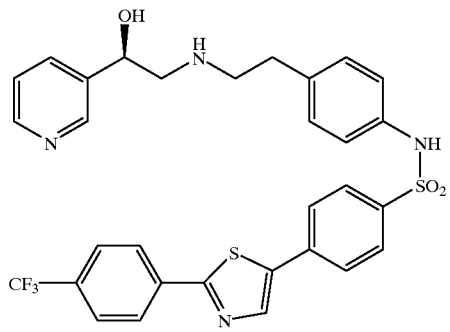

(R)-N-[4-[2-[[2-Hydroxy-2-(pyridin-3-yl)ethyl]amino]ethyl]phenyl]-4-[2-(4-trifluoromethylphenyl)thiazol-5-yl]benzenesulfonamide Step A. α-Amino-4-bromoacetophenone hydrochloride The general procedure for the modified Delepine reaction (Goddard, C. J. J. Heterocyclic Chem. 1991, 28, 17) was used. A mixture of α,4-dibromoacetophenone (2.78 g) and hexamethylenetetramine (1.47 g) in 40 mL of chloroform was stirred vigorously overnight. The precipitated solid was collected, washed with chloroform, dried in vacuo, and was then suspended in a mixture of 6 mL of concentrated hydrochloric acid and 30 mL of methanol and stirred overnight. The precipitated solid was collected, washed with methanol and dried in vacuo, affording 1.38 g of white powder, which was used without further purification.

Step B. α-Amino-4-bromoacetophenone 4-(Trifluoromethyl)benzamide

A mixture of the above hydrochloride salt (1.38 g) and triethylamine (1.50 mL) in 40 mL of chloroform was cooled in an ice-water bath, and a solution of 4-(trifluoromethyl) benzoyl chloride (1.21 g) in 5 mL of chloroform was added dropwise. The mixture was stirred at 0° C. for 1 h, diluted with 30 mL of chloroform and washed sequentially with water, 5% aqueous hydrochloric acid, saturated aqueous sodium bicarbonate and saturated brine. Drying and removal of solvent under reduced pressure afforded an off-white solid, which was triturated with ethyl acetate:hexane (6:1), collected, and dried, affording 1.20 g of the title compound as a white solid: mp 173–174° C.; $^1$H NMR (400 MHz, CDCl$_3$) δ 7.96 (d, J=8.0 Hz, 2H), 7.87 (d, J=8.6 Hz, 2H), 7.72 (d, J=8.0 Hz, 2H), 7.67 (d, J=8.6 Hz, 2H), 4.92 (apparent d, J=4.3 Hz, 2H); FAB MS m/z 387.4 (M+1).

Step C. 5-(4-Bromophenyl)-2-(4-Trifluoromethylphenyl)thiazole

A mixture of the amide from Step B above (0.386 g) and Lawesson's reagent (0.410 g) in 6 mL of dry toluene was warmed at reflux for 1.5 h. The solution was cooled and applied directly to a silica gel column. Sequential elution with hexane and then 10% ethyl acetate:hexane provided 0.380 g of the title compound as a white solid: $^1$H NMR (400 MHz, CDCl$_3$) δ 8.05 (d, J=8.5 Hz, 2H), 8.03 (s, 1H), 7.69 (d, J=8.5 Hz, 2H), 7.55 (d, J=8.6 Hz, 2H), 7.45 (d, J=8.6 Hz, 2H); FAB MS m/z 385.9 (M+1).

Step D. 5-(4-Chlorosulfonylphenyl)-2-(4-Trifluoromethylphenyl)thiazole

A solution of the above aryl bromide (0.356 g) in 6 mL of dry THF was treated with n-butyllithium (0.63 mL of 1.6 M in hexanes), followed by sulfur dioxide and then N-chlorosuccinimide as described in Example 1, Step C above. The crude sulfonyl chloride obtained (0.171 g) was used without further purification: $^1$H NMR (400 MHz, CDCl$_3$) δ 8.09 (d, J=8.5 Hz, 2H), 8.05 (s, 1H), 7.58 (m, 4H), 7.45 (d, J=8.6 Hz, 2H).

Step E. (R)-N-[4-[2-[[2-Hydroxy-2-(pyridin-3-yl)ethyl]amino]ethyl]phenyl]-4-[2-(4-trifluoromethylphenyl)thiazol-5-yl]benzenesulfonamide A solution of 0.131 g of (R)-N-[2-[4-(aminophenyl)]ethyl]-2-hydroxy-2-(pyrid-3-yl)ethylcarbamic acid 1,1-dimethylethyl ester in 1.6 mL of dichloromethane was treated with the above sulfonyl chloride (0.171 g) and 0.040 mL of pyridine, followed by addition of trifluoroacetic acid, as described in Example 1, Step D. The crude product was purified by flash chromatography on silica gel (9:1 dichloromethane:10% NH$_4$OH/MeOH eluant) to afford 0.227 g of the title compound as a light yellow foam: $^1$H NMR (400 MHz, CD$_3$OD) δ 8.50 (d, J=2.1 Hz, 1H), 8.40 (dd, J=5.0 and 1.6 Hz, 1H), 8.27 (s, 1H), 8.14 (d, J=8.0 Hz, 2H), 7.79 (m, 7H), 7.09 (d, J=8.6 Hz, 2H), 7.04 (d, J=8.6 Hz, 2H), 4.78 (dd, J=7.3 and 5.2 Hz, 1H), 2.7–2.9 (m, 6H). FAB MS m/z 625.3 (M+1).

EXAMPLE 4

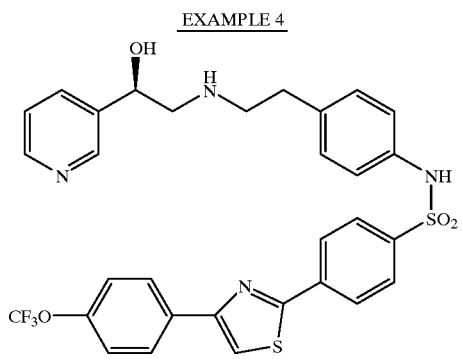

(R)-N-[4-[2-[[2-Hydroxy-2-(pyridin-3-yl)ethyl]amino]ethyl]phenyl]-4-[4-(4-trifluoromethoxyphenyl)thiazol-2-yl]benzenesulfonamide The title compound was prepared according to the procedure outlined in Example 2: $^1$H NMR (400 MHz, CD$_3$OD) δ 8.52 (d, J=2.0 Hz, 1H), 8.43 (dd, J=4.9 and 1.6 Hz, 1H), 8.12 (d, J=8.5 Hz, 2H), 8.10 (d, J=8.6 Hz, 2H), 7.98 (s, 1H), 7.83 (overlapping d, J=8.5 Hz, 2H and m, 1H), 7.38 (dd, J=7.9 and 5.0 Hz, 1H), 7.33 (d, J=8.6 Hz, 2H), 7.12 (d, J=8.5 Hz, 2H), 7.07 (d, J=8.5 Hz, 2H), 4.85 (dd, J=8.8 and 4.2 Hz, 1H), 2.7–3.1 (m, 6H). FAB MS m/z 641 (M+1).

Following the procedures outlined for Examples 1 and 2, the compounds listed in Table 1 were prepared.

TABLE 1

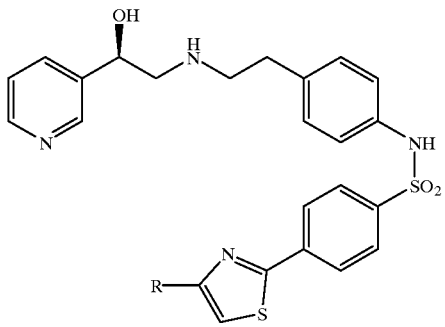

| Example | R | Selected $^1$H NMR (CD$_3$OD) |
|---|---|---|
| 5 | 3,4-difluorophenylmethyl | 7.97(d, J=7.0Hz, 2H), 7.76(d, J=7.8Hz, 1H), 7.24(s, 1H), 7.12–7.2(overlapping m, 2H, and d, J=7.0Hz, 2H), 3.86(s, 2H). |
| 6 | 3-pyridyl | 9.16(s, 1H), 8.49(m, 2H), 8.40(m, 2H), 8.11(overlapping d, J=8.5 Hz, 2H and s, 1H), 7.82(d, J=8.5 Hz, 2H), 7.78(d, J=7.9Hz, 1H), 7.49(dd, J=8.4 and 4.8Hz, 1H), 7.36(dd, J=7.9 and 5.0Hz, 1H). |
| 7 | 4-fluorophenylmethyl | 7.98(d, J=8.6Hz, 2H), 7.77(d, J=8.6Hz, 2H), 7.28(dd, J=8.5 and 5.5Hz, 2H), 7.18(s, 1H), 6.96–7.10 (m, 6H), 4.11(s, 2H). |
| 8 | 3,4-difluorophenyl | 8.09(d, J=8.6Hz, 2H), 7.94(s, 1H), 7.91(m, 1H), 7.75–7.85 (overlapping d, J=8.6Hz, 2H and m, 2H), 7.25–7.38(m, 2H). |
| 9 | 4-(trifluoromethyl)-phenylmethyl | 7.99(d, J=8.5Hz, 2H), 7.76(d, J=8.5Hz, 2H), 7.58(d, J=8.1Hz, 2H), 7.46(d, J=8.1Hz, 2H), 7.27 (s, 1H), 4.22(s, 2H). |
| 10 | 2-pyridyl | 8.56(d, J=4.8Hz, 1H), 8.21 |

TABLE 1-continued

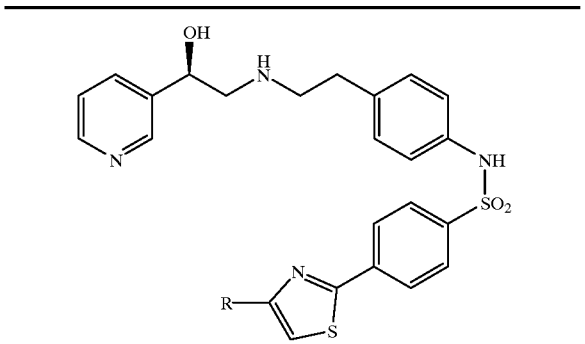

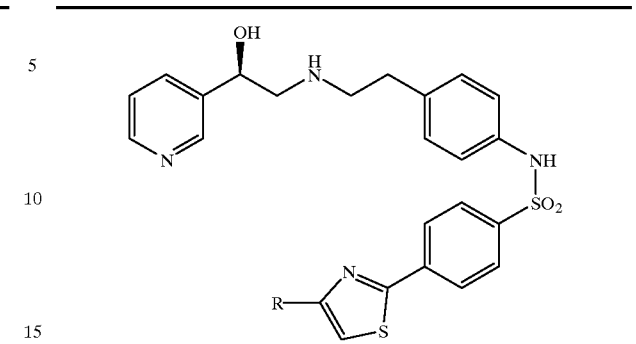

| Example | R | Selected ¹H NMR (CD₃OD) |
|---|---|---|
| | | (overlapping s, 1H and m, 1H), 8.12 (d, J=8.6Hz, 2H), 7.88(m, 1H), 7.80(overlapping d, J=8.6Hz, 2H and m, 1H), 7.36(m, 2H). |
| 11 | 1-(2-phenyl)ethyl | 8.01(d, J=8.3Hz, 2H), 7.78 (overlapping d, J=8.3Hz, 2H and m, 1H), 7.15–7.25(m, 6H), 3.06 (m, 4H). |
| 12 | 4-fluorophenyl | 8.10(d, J=8.3Hz, 2H), 8.00(dd, J=8.8 and 5.4Hz, 2H), 7.85(s, 1H), 7.81(d, J=8.3Hz, 2H), 7.14 (apparent t, J=8.8Hz, 2H). |
| 13 | 2-naphthyl | 8.12(d, J=8.6Hz, 2H), 8.04(dd, J=8.6 and 1.7Hz, 1H), 7.98(s, 1H), 7.80–7.95(overlapping d, J=8.6 Hz, 2H and m, 4H), 7.77(d, J=7.9 Hz, 1H), 7.46(m, 2H). |
| 14 | 3,4,5-trifluorophenyl | 8.07(d, J=8.6Hz, 2H), 8.01(s, 1H), 7.81(d, J=8.6Hz, 2H), 7.76 (dd, J=9.3 and 6.7Hz, 2H). |
| 15 | 4-hexylphenyl | 8.06(d, J=8.4Hz, 2H), 7.94(d, J=8.4Hz, 2H), 7.79(m, 3H), 7.23 (d, J=8.6Hz, 2H), 2.62(t, J=7.5 Hz, 2H), 1.61(m, 2H), 1.27(m, 6H), 0.89(t, J=7.3Hz, 3H). |
| 16 | 4-(trifluoromethoxy)-phenylmethyl | 7.99(d, J=8.6Hz, 2H), 7.77(d, J=8.6Hz, 2H), 7.37(d, J=8.4Hz, 2H), 7.24(s, 1H), 7.18(d, J=8.4 Hz, 2H), 4.16(s, 2H). |
| 17 | 4-(trifluoromethoxy)-phenoxymethyl | 8.05(d, J=8.5Hz, 2H), 7.80(d, J=8.5Hz, 2H), 7.67(s, 1H), 7.20(d, J=8.7Hz, 2H), 7.07(m, 6H), 5.22 (s, 2H) |
| 18 | 2-benzo[b]thienyl | 8.08(d, J=8.4Hz, 2H), 7.80(m, 5H), 7.32(m,3H). |
| 19 | 3-quinolinyl | 9.42(s, 1H), 8.84(s, 1H), 8.19(s, 1H), 8.10(d, J=8.6Hz, 2H), 7.97 (m, 2H), 7.83(d, J=8.6Hz, 2H), 7.73(apparent t, J=7.0Hz, 1H), 7.60(apparent t, J=7.0Hz, 1H). |
| 20 | 6-quinolinyl | 8.84(d, J=4.2Hz, 1H), 8.62(s, 1H), 8.40(m, 2H), 8.18(d, J=8.6 Hz, 2H), 8.16(s, 1H), 8.08(d, J=9.1Hz, 1H), 7.85(d, J=8.6Hz, 2H), 7.56(m, 1H). |
| 21 | 2-benzo[b]furyl | 8.06(d, J=8.6Hz, 2H), 7.82(d, J=8.6Hz, 2H), 7.81(s, 1H), 7.58(d, J=7.1Hz, 1H), 7.47(d, J=8.3Hz, 1H), 7.28(m, 2H), 7.22(s, 1H). |
| 22 | 3-indolyl | 8.10(d, J=8.6Hz, 2H), 8.05(d, J=6.9Hz, 1H), 7.80(d, J=8.6Hz, 2H), 7.78(s, 1H), 7.65(s, 1H), 7.40 (d, J=6.8Hz, 1H), 7.16(m, 1H). |
| 23 | 2,4-difluorophenyl | 8.27(m, 1H), 8.10(d, J=8.6Hz, 2H), 7.86(s, 1H), 7.81(d, J=8.6 Hz, 2H), 7.05(m, 6H). |
| 24 | 3,5-difluorophenyl | 8.12(d, J=8.4Hz, 2H), 8.08(s, 1H), 7.83(d, J=8.4Hz, 2H), 7.62 (dd, J=8.8 and 2.3Hz, 2H), 6.93 (tt, J=8.8 and 2.3Hz, 1H). |
| 25 | 4-(1,1-dimethylethyl)phenyl | 8.05(d, J=8.5Hz, 2H), 7.83(d, J=8.5Hz, 2H), 7.79(d, J=8.5Hz, 2H), 7.57(s, 1H), 7.42(d, J=8.5 Hz, 2H), 1.32(s, 9H). |
| 26 | 2,3-difluorophenyl | 8.12(d, J=8.4Hz, 2H), 8.03(m, 1H), 8.01(d, J=2.2Hz, 1H), 7.82 (d, J=8.4Hz, 2H), 7.25(m, 2H), |
| 27 | 3-(trifluoromethyl)-phenyl | 8.31(s, 1H), 8.25(d, J=6.5Hz, 1H), 8.13(d, J=8.5Hz, 2H), 8.09 (s, 1H), 7.83(d, J=8.5Hz, 2H), 7.62(m, 2H). |
| 28 | 4-(difluoromethyl)-phenyl | 8.12(d, J=8.6Hz, 2H), 8.03(d, J=8.7Hz, 2H), 7.89(s, 1H), 7.81(d, J=8.6Hz, 2H), 7.19(d, J=8.7Hz, 2H), 6.87(t, J=73Hz, 1H). |
| 29 | 2,4-dichlorophenyl | 8.09(d, J=8.6Hz, 2H), 8.07(s, 1H), 7.96(d, J=8.4Hz, 1H), 7.81 (d, J=8.6Hz, 2H), 7.57(s, 1H), 7.40(d, J=8.5Hz, 1H). |
| 30 | 2-(trifluoromethyl)-phenyl | 8.08(d, J=8.6Hz, 2H), 7.84(m, 2H), 7.82(d, J=8.6Hz, 2H), 7.69 (m, 3H); 7.61(m, 1H). |
| 31 | 2-fluoro-4-(trifluoromethyl)-phenyl | 8.47(m, 1H), 8.13(d, J=8.6Hz, 2H), 8.11(d, J=2.3Hz, 1H), 7.83 (d, J=8.6Hz, 2H), 7.59(s, 1H), 7.56(d, J=5.0Hz, 1H). |
| 32 | 4-fluoro-2-(trifluoromethyl)-phenyl | 8.07(d, J=8.6Hz, 2H), 7.80(d, J=8.6Hz, 2H), 7.73(dd, J=8.4 and 5.5Hz, 1H), 7.70(s, 1H); 7.59(dd, J=9.2 and 2.8Hz, 1H), 7.46 (apparent td, J=8.6 and 2.8Hz, 1H). |
| 33 | 2,4-bis(trifluoromethyl)-phenyl | 8.10(m, 3H), 8.02(d, J=8.0Hz, 1H), 7.95(d, J=8.3Hz, 1H), 7.81 (m, 4H). |
| 34 | 4-biphenyl | 8.08(d, J=8.6Hz, 2H), 8.00(d, J=8.5Hz, 2H), 7.80(d, J=8.6Hz, 2H), 7.70–7.73(m, 2H), 7.64(d, J=8.5Hz, 2H), 7.61(d, J=7.2Hz, 2H), 7.42(t, J=7.2Hz, 2H), 7.25–7.35(m, 2H). |
| 35 | 3,4-dihydroxyphenyl | 8.07(d, J=8.6Hz, 2H), 7.79–7.83 (m, 3H), 7.79(s, 1H), 7.57(s, 1H), 7.41(d, J=2.1Hz, 1H), 7.31(dd, J=8.2 and 2.1Hz, 1H), 6.81(d, J=8.2Hz, 2H). |
| 36 | 4-hydroxyphenyl | 8.09(d, J=8.5Hz, 2H), 7.77–7.83 (m, 4H), 7.67(s, 1H), 6.82(d, J=8.7Hz, 2H). |
| 37 | 4-acetoxyphenyl | 8.08(d, J=8.6Hz, 2H), 7.97(d, J=8.8Hz, 2H), 7.80(d, J=8.6Hz, 2H), 7.74(s, 1H), 7.14(d, J=8.8Hz, 2H), 2.30(s, 3H). |
| 38 | 4-acetamidophenyl | 8.11(d, J=8.5Hz, 2H), 7.93(d, J=8.7Hz, 2H), 7.77–7.83(m, 4H), 7.62(d, J=8.7Hz, 2H), 2.14(s, 3H). |

EXAMPLE 39

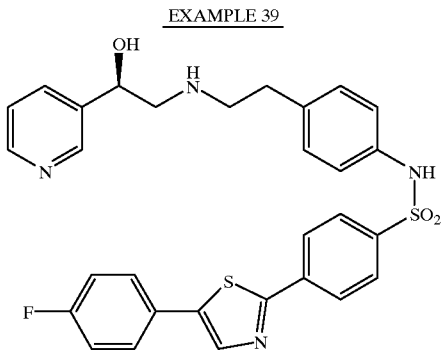

(R)-N-[4-[2-[[2-Hydroxy-2-(pyridin-3-yl)ethyl]amino] ethyl]phenyl]-4-[5-(4-fluorophenyl)thiazol-2-yl] benzenesulfonamide Step A. 2-Bromo-2-(4-fluorophenyl)ethanal To a solution of 672 mg of o-iodoxybenzoic acid in methyl sulfoxide (5 mL) was added 250 μL of 2-(4-fluorophenyl)ethanol and stirring was continued for 3 h. Water (20 mL) was added and the reaction mixture filtered, the filtrate was extracted with ether (3×20 mL), washed with brine (10 mL), dried over magnesium sulfate, and concentrated to give 2-(4-fluorophenyl) ethanal as an unstable oil. The material was immediately dissolved in acetonitrile (3.5 mL) at 0° C. and 264 μL of bromotrimethylsilane and 142 μL of methyl sulfoxide were added. After stirring for 1 h, water (10 mL) was added and the reaction mixture was extracted with ether (3×20 mL), washed with brine (10 mL), dried over magnesium sulfate, and concentrated to give the title compound (220 mg) as an unstable oil which was used immediately without further purification.

Step B (R)-N-[4-[2-[[2-Hydroxy-2-(pyridin-3-yl)ethyl] amino]ethyl]phenyl]-4-[5-(4-fluorophenyl)thiazol-2-yl] benzenesulfonamide A mixture of 50 mg of thioamide from Example 2, step A and 220 mg of 2-bromo-2-(4-fluorophenyl)ethanal in chloroform/acetonitrile (2/1 1.5 mL) was warmed at reflux for 16 h. The cooled reaction mixture was concentrated under reduced pressure and purified by preparative thin layer chromatography (9:1 dichloromethane/methanol eluant) to give (R)-N-[4-[2-[N-(1,1-dimethylethoxycarbonyl)-N-[2-hydroxy-2-(pyridin- 3-yl)ethyl]amino]ethyl]phenyl]-4-[5-(4-fluorophenyl)thiazol-2-yl]benzenesulfonamide (12 mg). This was dissolved in 2 mL of dichloromethane and 2 mL of trifluoroacetic acid (TFA). After stirring for 2 h at ambient temperature, the solution was concentrated under reduced pressure. Residual TFA was removed by azeotropic distillation with dichloromethane, and the residue was purified by preparative thin layer chromatography (9:1 dichloromethane/10% NH$_4$OH in methanol eluant) and then preparative reverse phase HPLC (65/35 methanol/10% TFA in water eluant) affording the title compound (5.0 mg). $^1$H NMR (400 MHz, CD$_3$OD) δ 8.75 (m, 1H), 8.66 (m, 1H), 8.13 (s, 1H), 8.06 (d, J=8 Hz, 2H), 7.85 (d, J=8 Hz, 2H), 7.79–7.69 (m, 3H), 7.22–7.09 (m, 6H), 5.16–5.10 (m, 1H), 3.30–3.17 (m, 4H), 2.98–2.91 (m, 2H).

EXAMPLE 40

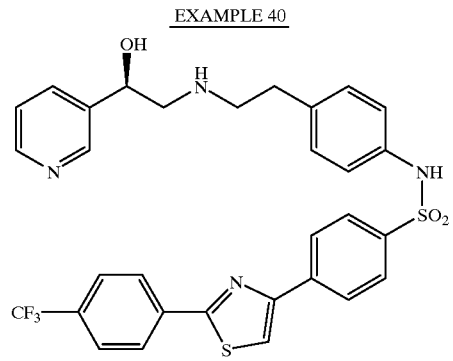

(R)-N-[4-[2-[[2-Hydroxy-2-(pyridin-3-yl)ethyl]amino] ethyl]phenyl]-4-[2-(4-trifluoromethylphenyl)thiazol-4-yl] benzenesulfonamide Step A. 4-(Trifluoromethyl)thiobenzamide 4-(Trifluoromethyl)benzonitrile (3.42 g) was treated with triethylamine (2.12 g) and hydrogen sulfide in pyridine solution as described in Example 2, Step A. The crude product was triturated with hexane (150 mL) and collected to afford 3.80 g of yellow powder: mp 133–136° C.; $^1$H NMR (400 MHz, CDCl$_3$) δ 7.92 (d, J=8.4 Hz, 2H), 7.64 (d, J=8.4 Hz, 2H).

Step B. 4-(4-Bromophenyl)-2-(4-Trifluoromethylphenyl) thiazole

A solution of the above thioamide (0.41 g) and α,4-dibromoacetophenone (0.56 g) in 5 mL of absolute ethanol was warmed at reflux for 14 h. The reaction mixture was cooled in ice, and the solid was collected and washed with ethanol, affording 0.67 g of a white, crystalline solid: mp 143–144° C.; $^1$H NMR (400 MHz, CDCl$_3$) δ 8.12 (d, J=7.9 Hz, 2H), 7.85 (d, J=8.5 Hz, 2H), 7.70 (d, J=7.9 Hz, 2H), 7.56 (d, J=8.5 Hz, 2H), 7.53 (s, 1H); FAB MS m/z 386.1 (M+1).

Step C. 4-(4-Bromophenyl)-2-(4-Trifluoromethylphenyl)-5-(trimethylsilyl)thiazole A solution of the aryl bromide obtained above (0.576 g) in 10 mL of dry tetrahydrofuran (THF) was cooled in a dry ice-acetone bath, and a solution of n-butyllithium (1.0 mL of 1.6 M in hexanes) was added dropwise. After an additional 10 min, trimethylsilyl chloride (0.196 g, 0.23 mL) was added in one portion. After an additional 15 min, the cooling bath was removed, and the reaction mixture was allowed to warm to room temperature over 1 h. Saturated aqueous ammonium chloride (1 mL) was added, and the mixture was concentrated under reduced pressure. Ether-water partition-washing afforded a white, waxy solid, which was purified by flash chromatography on a silica gel column (5% ethyl acetate-hexane eluant) to provide 0.49 g of the title compound as a white solid: mp 88–89° C.; $^1$H NMR (400 MHz, CDCl$_3$) δ 8.09 (d, J=8.1 Hz, 2H), 7.67 (d, J=8.1 Hz, 2H), 7.56 (d, J=8.6 Hz, 2H), 7.49 (d, J=8.6 Hz, 2H), 0.25 (s, 9H); FAB MS m/z 458.0 (M+1).

Step D. 4-(4-Chlorosulfonylphenyl)-2-(4-Trifluoromethylphenyl)-5-(trimethylsilyl)thiazole The aryl bromide from above (0.456 g) was treated with n-butyllithium, followed by sulfur dioxide and then N-chlorosuccinimide as described in Example 1, Step C above. The crude product (0.223 g) was used without further purification.

Step E. (R)-N-[4-[2-[[2-Hydroxy-2-(pyridin-3-yl)ethyl] amino]ethyl]phenyl]-4-[2-(4-trifluoromethylphenyl)thiazol-4-yl]benzenesulfonamide A solution of 0.150 g of (R)-N-[2-[4-(aminophenyl)] ethyl]-2-hydroxy-2-(pyrid-3-yl)ethylcarbamic acid 1,1- dimethylethyl ester (Fisher, et. al., U.S. Pat. No. 5,561,142, Oct. 1, 1996) in 1.6 mL of dichloromethane was treated with the above sulfonyl chloride (0.223 g) and 0.040 mL of pyridine, followed by addition of trifluoroacetic acid, as described in Example 1, Step D. The crude product was purified by flash chromatography on silica gel (9:1 dichloromethane:10% ammonium hydroxide/methanol eluant) to afford 0.171 g of a light yellow foam, which was dissolved in 2 mL of acetonitrile and treated with a 15% solution of HF in acetonitrile. The mixture was stirred at room temperature for 1.5 h, and was then concentrated under reduced pressure. The crude product was purified by flash chromatography on a silica gel column (9:1 dichloromethane:10% ammonium hydroxide/methanol eluant) to afford 0.091 g of the title compound as a light yellow foam: $^1$H NMR (400 MHz, CD$_3$OD) δ 8.49 (d, J=2.1 Hz, 1H), 8.40 (dd, J=4.9 and 1.6 Hz, 1H), 8.19 (d, J=7.7 Hz, 2H), 8.11 (d, J=8.6 Hz, 2H), 8.05 (s, 1H), 7.78 (apparent t, J=8.5 Hz, 4H), 7.35 (dd, J=5.0 and 7.9, 1H), 7.09 (d, J=8.6 Hz, 2H), 7.04 (d, J=8.6 Hz, 2H), 4.77 (dd, J=7.4 and 5.2 Hz, 1H), 2.7–2.9 (m, 6H); FAB MS m/z 625.3 (M +1).

EXAMPLE 41

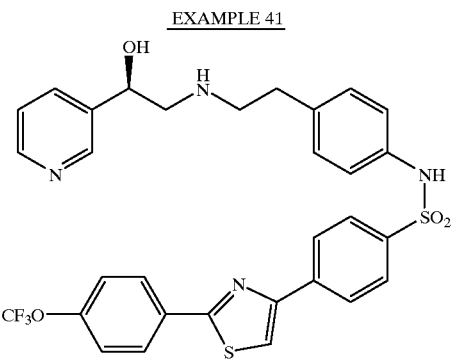

(R)-N-[4-[2-[[2-Hydroxy-2-(pyridin-3-yl)ethyl]amino]ethyl]phenyl]-4-[2-(4-trifluoromethoxyphenyl)thiazol-4-yl]benzenesulfonamide The title compound was prepared according to the procedure outlined in Example 40: $^1$H NMR (400 MHz, CD$_3$OD) δ 8.50 (d, J=2.1 Hz, 1H), 8.40 (dd, J=4.9 and 1.6 Hz, 1H), 8.11 (d, J=2.9 Hz, 2H), 8.09 (d, J=2.9 Hz, 2H), 7.99 (s, 1H), 7.78 (apparent d, J=8.7 Hz, 3H), 7.37 (apparent d, J=8.7 Hz, 2H), 7.35 (m, 1H), 7.09 (d, J=8.7 Hz, 2H), 7.04 (d, J=8.7 Hz, 2H), 4.76 (dd, J=7.4 and 5.1 Hz, 1H), 2.7–2.9 (m, 6H); FAB MS m/z 641.3 (M +1).

What is claimed is:

1. A compound having the formula I:

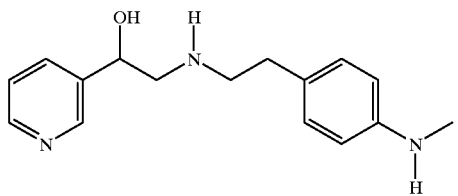

I

-continued

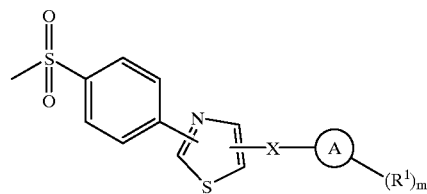

wherein
X is
  (1) a bond;
m is
  0 to 5;
A is
  (1) phenyl, or
  (2) a benzene ring fused to a $C_5$–$C_{10}$ carbocyclic ring;
$R^1$ is
  (1) $C_1$–$C_{10}$ alkyl optionally substituted with up to 5 groups selected from
    (a) hydroxy,
    (b) halogen,
    (c) cyano,
    (d) $QR^2$,
    (e) $C_3$–$C_8$ cycloalkyl,
    (f) A optionally substituted with up to 5 groups selected from halogen, $C_1$–$C_{10}$ alkyl and $C_1$–$C_{10}$ alkoxy,
    (g) $Q'COR^3$,
    (h) $S(O)_nR^3$, where n is 0 to 2,
    (i) $NR^2SO_2R^3$,
    (j) $NR^2CO_2R^2$, and
    (k) $CO_2R^2$,
  (2) $C_3$–$C_8$ cycloalkyl,
  (3) halogen,
  (4) cyano,
  (5) $QR^2$,
  (6) $S(O)_nR^3$, where n is 0 to 2,
  (7) $Q'COR^3$,
  (8) $NR^2SO_2R^3$,
  (9) $NR^2CO_2R^2$,
  (10) A optionally substituted with up to 5 groups independently selected from
    (a) $R^2$,
    (b) $QR^2$, and
    (c) halogen; or
  (11) $CO_2R^2$;
$R^2$ is
  (1) hydrogen,
  (2) $C_1$–$C_{10}$ alkyl optionally substituted with up to 5 groups selected from
    (a) hydroxy,
    (b) halogen,
    (c) $CO_2R^4$,
    (d) $S(O)_n$-$C_1$–$C_{10}$ alkyl, where n is 0 to 2,
    (e) $C_3$–$C_8$ cycloalkyl,
    (f) $C_1$–$C_{10}$ alkoxy, and
    (g) A optionally substituted with up to 5 groups selected from halogen, $C_1$–$C_{10}$ alkyl and $C_1$–$C_{10}$ alkoxy,
  (3) $C_3$–$C_8$ cycloalkyl, or
  (4) A optionally substituted with up to 5 groups selected from
    (a) halogen,
    (b) nitro, (c) NR⁴R⁴,
(d) $C_1$–$C_{10}$ alkoxy,
(e) $S(O)_n$-$C_1$–$C_{10}$ alkyl where n is 0 to 2, and
(f) $C_1$–$C_{10}$ alkyl optionally substituted with up to 5 groups selected from hydroxy, halogen, $CO_2R^4$, $S(O)_n$-$C_1$–$C_{10}$ alkyl, where n is 0 to 2, $C_3$–$C_8$ cycloalkyl, $C_1$–$C_{10}$ alkoxy, and A optionally substituted with up to 5 groups selected from halogen, $C_1$–$C_{10}$ alkyl and $C_1$–$C_{10}$ alkoxy;

$R^3$ is
(1) $R^2$ or
(2) $NR^2R^2$;

$R^4$ is
(1) H, or
(2) $C_1$–$C_{10}$ alkyl;

Q is
(1) $N(R^2)$,
(2) O or
(3) $S(O)_n$, and n is 0 to 2;

Q' is
(1) $N(R^2)$,
(2) O or
(3) a bond; or a pharmaceutically acceptable salt thereof or a prodrug thereof.

2. A compound of claim 1 wherein
$R^1$ is
(1) $C_1$–$C_{10}$ alkyl optionally substituted with up to 5 halogens;
(2) halogen,
(3) $QR^2$,
(4) $Q'COR^3$,
(5) phenyl;

$R^2$ is
(1) hydrogen,
(2) $C_1$–$C_{10}$ alkyl optionally substituted with up to 5 halogens;

$R^3$ is
(1) $C_1$–$C_{10}$ alkyl; and

Q is
(1) O.

3. A compound of claim 1 wherein
X is
(1) a bond;
m is
0 to 5;
A is
(1) phenyl, or
(2) a benzene ring fused to a $C_5$–$C_{10}$ carbocyclic ring;

$R^1$ is
(1) $C_1$–$C_{10}$ alkyl optionally substituted with up to 5 halogens;
(2) halogen,
(3) $QR^2$,
(4) $Q'COR^3$,
(5) phenyl;

$R^2$ is
(1) hydrogen,
(2) $C_1$–$C_{10}$ alkyl optionally substituted with up to 5 halogens;

$R^3$ is
(1) $C_1$–$C_{10}$ alkyl; and

Q is
(1) O.

4. A compound of claim 1 wherein either the benzenesulfonamide moiety or A is attached to the C2 of the thiazole ring, and the other to the C4 positions of the thiazole ring.

5. A compound of claim 4 wherein
X is
(1) a bond;
m is
0 to 5;
A is
(1) phenyl, or
(2) naphthyl;

$R^1$ is
(1) $C_1$–$C_{10}$ alkyl optionally substituted with up to 5 halogens;
(2) halogen,
(3) $QR^2$,
(4) $Q'COR^3$,
(5) phenyl;

$R^2$ is
(1) hydrogen,
(2) $C_1$–$C_{10}$ alkyl optionally substituted with up to 5 halogens;

$R^3$ is
(1) $C_1$–$C_{10}$ alkyl; and

Q is
(1) O.

6. A compound of claim 5 wherein A is selected from the group consisting of phenyl and naphthyl.

7. A compound of claim 1 having the formula:

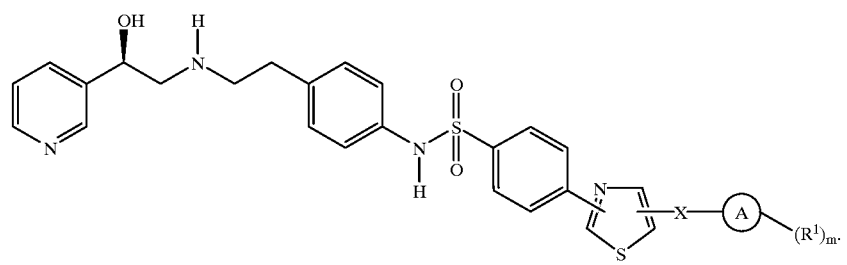

8. A compound selected from the group consisting of:
N-[4-[2-[[2-hydroxy-2-(pyridin-3-yl)ethyl]amino]ethyl]phenyl]-4-[4-[4-(trifluoromethyl)phenyl]thiazol-2-yl]benzenesulfonamide;

N-[4-[2-[[2-hydroxy-2-(pyridin-3-yl)ethyl]amino]ethyl]phenyl]-4-[4-(trifluoromethoxy)phenyl]thiazol-2-yl]benzenesulfonamide;

N-[4-[2-[[2-hydroxy-2-(pyridin-3-yl)ethyl]amino]ethyl]phenyl]-4-[4-(3,4-difluorophenyl)thiazol-2-yl]benzenesulfonamide;

N-[4-[2-[[2-hydroxy-2-(pyridin-3-yl)ethyl]amino]ethyl]phenyl]-4-[4-(4-fluorophenyl)thiazol-2-yl]benzenesulfonamide;

N-[4-[2-[[2-hydroxy-2-(pyridin-3-yl)ethyl]amino]ethyl]phenyl]-4-[4-(2-naphthyl)thiazol-2-yl]benzenesulfonamide;

N-[4-[2-[[2-hydroxy-2-(pyridin-3-yl)ethyl]amino]ethyl]phenyl]-4-[4-(3,4,5trifluorophenyl)thiazol-2-yl]benzenesulfonamide;

N-[4-[2-[[2-hydroxy-2-(pyridin-3-yl)ethyl]amino]ethyl]phenyl]-4-[4-(4-hexylphenyl)thiazol-2-yl]benzenesulfonamide;

N-[4-[2-[[2-hydroxy-2-(pyridin-3-yl)ethyl]amino]ethyl]phenyl]-4-[4-(2,4-difluorophenyl)thiazol-2-yl]benzenesulfonamide;

N-[4-[2-[[2-hydroxy-2-(pyridin-3-yl)ethyl]amino]ethyl]phenyl]-4-[4-(3,5-difluorophenyl)thiazol-2-yl]benzenesulfonamide;

N-[4-[2-[[2-hydroxy-2-(pyridin-3-yl)ethyl]amino]ethyl]phenyl]-4-[4-[4-(1,1-dimethylethyl)phenyl]thiazol-2-yl]benzenesulfonamide;

N-[4-[2-[[2-hydroxy-2-(pyridin-3-yl)ethyl]amino]ethyl]phenyl]-4-[4-(2,3-difluorophenyl)thiazol-2-yl]benzenesulfonamide;

N-[4-[2-[[2-hydroxy-2-(pyridin-3-yl)ethyl]amino]ethyl]phenyl]-4-[4-[3-(trifluoromethyl)phenyl]thiazol-2-yl]benzenesulfonamide;

N-[4-[2-[[2-hydroxy-2-(pyridin-3-yl)ethyl]amino]ethyl]phenyl]-4-[4-[4-(difluoromethyl)phenyl]thiazol-2-yl]benzenesulfonamide;

N-[4-[2-[[2-hydroxy-2-(pyridin-3-yl)ethyl]amino]ethyl]phenyl]-4-[4-(2,4-dichlorophenyl)thiazol-2-yl]benzenesulfonamide;

N-[4-[2-[[2-hydroxy-2-(pyridin-3-yl)ethyl]amino]ethyl]phenyl]-4-[4-[2-(trifluoromethyl)phenyl]thiazol-2-yl]benzenesulfonamide;

N-[4-[2-[[2-hydroxy-2-(pyridin-3-yl)ethyl]amino]ethyl]phenyl]-4-[4-[2-fluoro-4-(trifluoromethyl)phenyl]thiazol-2-yl]benzenesulfonamide;

N-[4-[2-[[2-hydroxy-2-(pyridin-3-yl)ethyl]amino]ethyl]phenyl]-4-[4-[4-fluoro-2-(trifluoromethyl)phenyl]thiazol-2-yl]benzenesulfonamide;

N-[4-[2-[[2-hydroxy-2-(pyridin-3-yl)ethyl]amino]ethyl]phenyl]-4-[4-[2,4-bis(trifluoromethyl)phenyl]thiazol-2-yl]benzenesulfonamide;

N-[4-[2-[[2-Hydroxy-2-(pyridin-3-yl)ethyl]amino]ethyl]phenyl]-4-[5-(4-fluorophenyl)thiazol-2-yl]benzenesulfonamide;

N-[4-[2-[[2-Hydroxy-2-(pyridin-3-yl)ethyl]amino]ethyl]phenyl]-4-[2-(4-trifluoromethylphenyl)thiazol-4-yl]benzenesulfonamide;

N-[4-[2-[[2-Hydroxy-2-(pyridin-3-yl)ethyl]amino]ethyl]phenyl]-4-[2-(4-trifluoromethylphenyl)thiazol-5-yl]benzenesulfonamide;

N-[4-[2-[[2-hydroxy-2-(pyridin-3-yl)ethyl]amino]ethyl]phenyl]-4-[4-(4-phenylphenyl)thiazol-2-yl]benzenesulfonamide;

N-[4-[2-[[2-hydroxy-2-(pyridin-3-yl)ethyl]amino]ethyl]phenyl]-4-[4-(3,4-dihydroxyphenyl)thiazol-2-yl]benzenesulfonamide;

N-[4-[2-[[2-hydroxy-2-(pyridin-3-yl)ethyl]amino]ethyl]phenyl]-4-[4-(4-hydroxyphenyl)thiazol-2-yl]benzenesulfonamide;

N-[4-[2-[[2-hydroxy-2-(pyridin-3-yl)ethyl]amino]ethyl]phenyl]-4-[4-(4-acetoxyphenyl)thiazol-2-yl]benzenesulfonamide;

N-[4-[2-[[2-hydroxy-2-(pyridin-3-yl)ethyl]amino]ethyl]phenyl]-4-[4-(4-acetamidophenyl)thiazol-2-yl]benzenesulfonamide; and N-[4-[2-[[2-hydroxy-2-(pyridin-3-yl)ethyl]amino]ethyl]phenyl]-4-[2-(4-trifluoromethoxyphenyl)thiazol-4-yl]benzenesulfonamide.

9. A composition for the treatment of diabetes or obesity or for lowering triglyceride or cholesterol levels or increasing high density lipoprotein levels or for decreasing gut motility or for reducing neurogenic inflammation or for treating depression or for treating gastrointestinal disorders which comprises an inert carrier and an effective amount of a compound of claim 1.

10. A pharmaceutical composition which comprises a compound of formula I and a pharmaceutically acceptable carrier.

* * * * *